US009545536B2

(12) United States Patent
Sato

(10) Patent No.: US 9,545,536 B2
(45) Date of Patent: Jan. 17, 2017

(54) TRAINING APPARATUS, CONTROL SEGMENT FOR TRAINING, AND CONTROL METHOD

(75) Inventor: Yoshiaki Sato, Tokyo (JP)

(73) Assignee: SATO SPORTS PLAZA CO., LTD., Tokyo (JP)

( * ) Notice: Subject to any disclaimer, the term of this patent is extended or adjusted under 35 U.S.C. 154(b) by 764 days.

(21) Appl. No.: 12/988,075

(22) PCT Filed: Apr. 16, 2009

(86) PCT No.: PCT/JP2009/058032
§ 371 (c)(1),
(2), (4) Date: Nov. 19, 2010

(87) PCT Pub. No.: WO2009/128561
PCT Pub. Date: Oct. 22, 2009

(65) Prior Publication Data
US 2011/0060231 A1 Mar. 10, 2011

(30) Foreign Application Priority Data

Apr. 17, 2008 (JP) ................................. 2008-108389

(51) Int. Cl.
*A61B 5/02* (2006.01)
*A63B 21/008* (2006.01)
(Continued)

(52) U.S. Cl.
CPC ....... *A63B 21/0023* (2013.01); *A61B 17/1355* (2013.01); *A63B 21/0085* (2013.01);
(Continued)

(58) Field of Classification Search
CPC .............. A61B 5/0285; A63B 21/0023; A63B 21/0085
(Continued)

(56) References Cited

U.S. PATENT DOCUMENTS 4,830,019 A * 5/1989 Shirasaki et al. ............. 600/494
2002/0120199 A1 * 8/2002 Ogura et al. ................. 600/485
(Continued)

FOREIGN PATENT DOCUMENTS

JP 2670421 B 6/1995
JP 09038051 A 2/1997
(Continued)

OTHER PUBLICATIONS

Japanese International Search Report and Written Opinion, PCT/JP2009/058032 (10 pages).

*Primary Examiner* — Patricia Mallari
*Assistant Examiner* — Tiffany Weston
(74) *Attorney, Agent, or Firm* — Edell, Shapiro & Finnan, LLC

(57) ABSTRACT

To provide a training apparatus for effective and safe performance of KAATSU training.
A training apparatus is made up of a tight fitting band 100, a main device 200, a measuring segment 300, and a control segment 400. The tight fitting band 100 is wrapped around a predetermined region of a limb. The tight fitting band 100 has an air-tight inflatable bag. The compression force applied to the limb can be varied by supplying the air to and removing the air from the inflatable bag. The main device 200 controls the supply and removal of the air into and from the inflatable bag. The measuring segment 300 is attached to the limb around which the tight fitting band 100 is wrapped to measure the magnitude of a pulse wave. The control segment 400 determines, in preprocessing performed before the KAATSU training, the pulse wave component at a time point at which the magnitude of the pulse wave reaches the maximum, and chooses, as an appropriate gas pressure, the pressure within the inflatable bag that is produced at a time point at which such a pulse wave is generated that is obtained by means of multiplying the pulse wave component
(Continued)

at a time point at which the magnitude of the pulse wave reaches the maximum with a numeral equal to or larger than 0.2 but smaller than 1.

20 Claims, 9 Drawing Sheets

(51) Int. Cl.
    *A63B 71/00*     (2006.01)
    *A63B 21/002*     (2006.01)
    *A61B 17/135*     (2006.01)
    *A63B 21/00*     (2006.01)
    *A63B 71/06*     (2006.01)
    *A63B 21/055*     (2006.01)

(52) U.S. Cl.
    CPC ...... *A63B 21/1449* (2013.01); *A63B 71/0622* (2013.01); *A63B 21/0552* (2013.01); *A63B 2071/0627* (2013.01); *A63B 2213/006* (2013.01); *A63B 2220/56* (2013.01); *A63B 2220/64* (2013.01); *A63B 2220/805* (2013.01); *A63B 2225/62* (2013.01); *A63B 2230/04* (2013.01); *A63B 2230/30* (2013.01)

(58) Field of Classification Search
    USPC ......... 600/490–503; 482/1, 4, 8, 9, 112, 113
    See application file for complete search history.

(56) References Cited

U.S. PATENT DOCUMENTS

| | | | |
|---|---|---|---|
| 2006/0128538 A1* | 6/2006 | Sato et al. | 482/112 |
| 2007/0049834 A1* | 3/2007 | Tao et al. | 600/494 |
| 2008/0243009 A1* | 10/2008 | Hersh et al. | 600/494 |
| 2008/0294021 A1* | 11/2008 | Lin et al. | 600/485 |

FOREIGN PATENT DOCUMENTS

| | | |
|---|---|---|
| JP | 2005006921 A | 1/2005 |
| JP | 2005058544 A | 3/2005 |
| JP | 2007125254 A | 5/2007 |
| JP | 2008099842 A | 5/2008 |

* cited by examiner

TRAINING APPARATUS, CONTROL SEGMENT FOR TRAINING, AND CONTROL METHOD

TECHNICAL FIELD

The present invention relates to a technique for performing a training method that has been practiced and spread as KAATSU training in a safer or more effective manner.

BACKGROUND ART

Mr. Yoshiaki Sato, the present inventor, has conducted studies for quite some time in order to develop a muscle strength increasing method for easy, safe, and effective muscle development, and put together the accomplishments into a patent application having Japanese Patent Application No. 5-313949, which has been granted as Japanese Patent No. 2670421.

The muscle strength increasing method according to the subject patent, which involves the application of pressure, is a distinctive non-conventional one. This muscle strength increasing method (hereinafter, referred to as "KAATSU training (registered trademark) method") is based on the following theoretical concept.

Muscles are composed of slow-twitch muscle fibers and fast-twitch muscle fibers. Slow-twitch muscle fibers are limited in their potential for growth. Accordingly, it is necessary to recruit fast-twitch muscle fibers of the slow- and fast-twitch muscle fibers in order to develop muscles. Recruitment of fast-twitch muscle fibers causes lactic acid buildup in the muscles, which triggers secretion of growth hormone from the pituitary. The growth hormone has effects of, for example, promoting muscle growth and shedding body fat. This means that recruitment and exhaustion of fast-twitch muscle fibers results in development of fast-twitch muscle fibers and, in turn, the entire muscles.

Slow-twitch muscle fibers and fast-twitch muscle fibers are different from each other in terms of the following. Slow-twitch muscle fibers use oxygen for energy and are recruited for low-intensity activities. Fast-twitch muscle fibers provide for activities regardless of whether or not oxygen is present. They are recruited after the slow-twitch muscle fibers for highly intense activities. Therefore, it is necessary to cause the earlier recruited and activated slow-twitch muscle fibers to be exhausted soon in order to recruit fast-twitch muscle fibers.

Conventional muscle strength increasing methods use heavy exercises with, for example, a barbell to cause the slow-twitch muscle fibers to be exhausted first, and then to recruit the fast-twitch muscle fibers. This recruitment of fast-twitch muscle fibers requires a significant amount of exercises, is time-consuming, and tends to increase the burden on muscles and joints.

On the other hand, muscle exercise may be performed under the condition of restricted blood flow into the limb distal to a predetermined location by means of applying pressure upon the muscles at the predetermined location near the top of the limb. Since less oxygen is supplied to these muscles, the slow-twitch muscle fibers, which require oxygen for energy, are thus exhausted in a short period of time. Muscle exercises with blood-flow restriction by application of pressure will result in recruitment of the fast-twitch muscle fibers without needing a large amount of exercises. More specifically, when a predetermined region near the top of a limb is compressed with pressure, venous circulation is restricted while arterial circulation is almost the same as the normal condition if an appropriate pressure is applied. This is because veins are closer to the skin surface of the limb while arteries are found deep within the limb. By holding that condition for a certain period of time, the limb that has compressed near the top thereof becomes engorged with blood which runs from arteries but cannot flow through veins. This condition is very close to the one achieved during heavy exercise of that limb. Consequently, the muscles get extremely exhausted. In addition, the muscle fatigue is also caused by the fact that the lactic acid that has built up in the muscles is less likely to be removed from the muscles because of the temporal occlusion of the veins.

A KAATSU training method can artificially provide a condition as described above that is similar to conditions obtained during and after exercises. This means that the KAATSU training method provides effects of muscle training and promotes secretion of growth hormone.

Based on the aforementioned mechanism, restriction of muscle blood flow can provide significant development of the muscles.

The KAATSU training method is premised on theoretical concept of muscle strength increase by the restriction of blood flow. More specifically, the KAATSU training method is intended to apply an appropriate compression force upon at least one of the limbs at a predetermined location near the top thereof, for the blood flow restriction into the limb distal to that location; put an appropriate stress attributed to blood flow decrease on the muscles, by the compression force; and thereby cause muscle fatigue. Thus, effective muscle development is achieved.

The KAATSU training method can compensate for a total amount of stress that is placed on the muscles by putting on the muscles a stress attributed to blood flow decrease. When combined with some exercises, the method advantageously reduces an exercise-related load as compared with conventional methods. This feature produces effects of reducing possible risks of joint- or muscle-damages and shortening a necessary time period for training, because it can decrease the amount of muscle exercises for the muscle development.

In addition, the KAATSU training method features muscle development without any exercises because it involves developing muscles by putting a stress attributed to blood flow decrease on the muscles. With this feature, the KAATSU training method is highly effective for the muscle development or for the recovery of motor ability in people with impaired motor function, e.g., the elders or an injured person.

When the KAATSU training is performed, it is very important how strong the proximal portion of the arm or the leg of the user is to be compressed.

The KAATSU training can achieve its effect only if it artificially provides conditions as if the arm or the leg of the user were doing heavy exercises, with blood-flow restriction by application of pressure to a proximal portion of the arm or the leg of the user. On the other hand, the KAATSU training can endanger the health of the user if the blood flow is excessively restricted.

However, at present, how large of a force is used to compress the arm or leg of the user is often determined by the person, relying on his or her knowledge and experience of the KAATSU training.

The present invention is directed to solve such problems and an object thereof is to provide a technique with which the KAATSU training can be used effectively, safely, and easily even by a person who has little skill of it.

SUMMARY OF THE INVENTION

In order to solve the aforementioned problems, the present inventor proposes the following invention. The invention associated with the present application can be broadly classified into a first invention and a second invention.

The first invention is a training apparatus comprising a tight fitting band including a belt having the length that is enough to be wrapped around a predetermined region of muscles of one of the limbs; fastening means for fastening said belt with said belt being wrapped around said predetermined region of muscles; and an inflatable bag provided in or on said belt, said inflatable bag being adapted to apply a predetermined compression pressure to said predetermined region of muscles by means of filling said inflatable bag with a gas to compress said predetermined region of muscles while said belt that has been wrapped around said predetermined region of muscles is fastened by said fastening means; pressure setting means that is capable of setting a gas pressure within said inflatable bag at a predetermined pressure; control means for controlling said pressure setting means in order to change said compression pressure; and pulse wave measuring means for measuring a predetermined parameter at a position near said predetermined region of muscles or a position closer to the distal end of the limb than said predetermined region of muscles, to generate a pulse wave data about the parameter, the parameter fluctuating along with the fluctuation of the magnitude of an arterial pulse wave that is changed in response to said compression pressure.

Said control means in this training apparatus is adapted to direct said pressure setting means to perform preprocessing and normal processing. Said control means is also adapted to, upon said preprocessing, control said pressure setting means so that said pressure setting means changes the gas pressure within said inflatable bag; determine a pulse wave component at a time point at which the maximum pulse wave pressure is produced after receiving a plurality of said pulse wave data from said pulse wave measuring means during the time period when the pressure within said inflatable bag is changing, the maximum pulse wave pressure being the gas pressure within said inflatable bag at a time point at which the amplitude of the pulse wave component reaches the maximum; and determine a first reference pressure which is the pressure within the inflatable bag at a time point when such a pulse wave component is produced that has an amplitude obtained by means of multiplying the amplitude of the pulse wave component at the time point at which said maximum pulse wave pressure is produced with a predetermined first coefficient that is equal to or larger than 0.2 but smaller than 1, the first reference pressure being larger than the pressure within said inflatable bag at the time point at which said maximum pulse wave pressure is produced. Said control means is adapted to, upon said normal processing, control said pressure setting means so that said pressure setting means keeps the gas pressure within said inflatable bag in a predetermined range above or below said the first reference pressure.

As described above, the KAATSU training involves in compressing a predetermined region near the top of the limb to cause the restriction of blood flow through the limb, thereby achieving an effect obtained as if it were doing exercises. The aforementioned compression or applying pressure is intended to produce temporal occlusion of the vein while keeping the arterial circulation through the limb, so that the limb that has compressed near the top thereof becomes engorged with blood.

More recently, for performing the KAATSU training, it has been found that a better outcome is often produced when such a pressure is applied to the predetermined region of the limb that occludes arteries to some extent as well as veins. However, excessive occlusion of the artery results in a decreased amount of blood flowing into the arm or leg, which can negatively affect the health of a person (user) who uses the KAATSU training.

In view of this, the training apparatus according to the first invention employs preprocessing prior to normal processing in which a proximal portion of the limb is actually compressed. This preprocessing is for determining the amplitude of a pulse wave component at a time point at which the maximum pulse wave pressure is produced which serves as an appropriate reference pressure to compress the limb near the top thereof. The maximum pulse wave pressure is determined according to the arterial pulse wave which fluctuates along with the compression of the limb near the top thereof with a varying pressure. It should be noted that the term "pulse wave" refers to a wave of energy that is caused when the heart contracts, blood is ejected into the aorta, and a resulting change in arterial blood pressure travels towards the peripheral blood vessels. A volume pulse wave is detected as a cross-section change in blood vessel due to the wave of energy. A pressure pulse wave is detected as a pressure change in blood vessel. In the first invention, a predetermined parameter that fluctuates along with the fluctuation of either of them (in the present invention, the predetermined parameter that fluctuates along with the fluctuation of the pulse wave includes the pulse wave itself) is detected by using the pulse wave measuring means to determine the aforementioned maximum pulse wave pressure.

The aforementioned maximum pulse wave pressure (more exactly, the pulse wave component at the time point at which the maximum pulse wave pressure is measured and the pressure within the inflatable bag at the time point at which the maximum pulse wave pressure is measured) can be used as a reference for determining an appropriate compression force. The reason is as follows.

The maximum pulse wave pressure is a gas pressure within the inflatable bag at the time point at which the varying pulse wave component reaches the maximum during the time period when the gas pressure within the inflatable bag of the tight fitting band is varied by the pressure setting means. Conversely, when the gas pressure within the inflatable bag is changed, the gas pressure within the inflatable bag at the time point at which the pulse wave component associated with the limb in question reaches the maximum is the maximum pulse wave pressure. The maximum pulse wave component indicates that a possibly maximum volume of arterial blood is flowing through that limb of which proximal portion has been compressed (or the arterial pumping function to force the blood is maximum). This has a certain degree of accuracy regardless of the user (e.g., irrespective of age or sex, general health, or athletic history). This is why the maximum pulse wave pressure can be used as a reference for determining the compression force to be applied to the proximal portion of the limb of the user.

Furthermore, according to the studies made by the present inventor, the compression force to be applied to the proximal portion of the limb of the user is the pressure within the inflatable bag at the time point at which such a pulse wave component is generated that is smaller than the pulse wave component at the time point at which the pressure within the inflatable bag reaches the maximum pulse wave pressure. A better outcome of the KAATSU training tends to be obtained when the pressure within the inflatable bag is larger than that for the pulse wave component at the time point at which the maximum pulse wave pressure is produced.

More specifically, in the first invention, upon preprocessing, the control means determines, by using the maximum pulse wave pressure as a reference, determine a first reference pressure which is the pressure within the inflatable bag at a time point when such a pulse wave component is produced that has an amplitude obtained by means of multiplying the amplitude of the pulse wave component at the time point at which said maximum pulse wave pressure is produced with a predetermined first coefficient that is equal to or larger than 0.2 but smaller than 1, the first reference pressure being larger than the pressure within said inflatable bag at the time point at which said maximum pulse wave pressure is produced. In addition, upon normal processing, the control means controls the pressure setting means so that the pressure setting means keeps the gas pressure within the inflatable bag in a predetermined range above or below the first reference pressure.

The reason why the definition of the first reference pressure includes "a pressure that is larger than the pressure within said inflatable bag at the time point at which said maximum pulse wave pressure is produced" is that the pulse wave exhibits a generally symmetric profile of fluctuation with respect to the pulse wave component (maximum pulse wave component) at the time point at which the pressure within the inflatable bag reaches the maximum pulse wave pressure wherein the lower the pressure within the inflatable bag becomes, the smaller the pulse wave components become on the side where the pressure within the inflatable bag is lower than the maximum pulse wave pressure and wherein the higher the pressure within the inflatable bag becomes, the smaller the pulse wave components become on the side where the pressure within the inflatable bag is higher than the maximum pulse wave pressure. The pressure that is equal to the first reference pressure appears twice, i.e., one on the side where the pressure is higher than the pressure within said inflatable bag at the time point at which said maximum pulse wave pressure is produced, and the other on the side where the pressure is lower than the pressure within said inflatable bag at the time point at which said maximum pulse wave pressure is produced. In addition, the reason why the aforementioned first coefficient is set to a numeral that is larger than 0.2 is that the pressure within the inflatable bag, if increased to a sufficient level to decrease pulse wave components to a size smaller than 0.2 times the maximum pulse wave component at the time point at which the maximum pulse wave pressure is produced, is more likely to be a cause of excessive arterial occlusion during the KAATSU training. This would possibly cause a trouble in safeness of the KAATSU training unless the user is a well-trained athlete.

The training apparatus according to the first invention contributes to improve the safeness and effect of the KAATSU training by means of keeping the pressure within the inflatable bag in a predetermined range above or below the first reference pressure. In addition, when the first coefficient is appropriately determined, then the first reference pressure, which serves as a reference pressure within the inflatable bag during the KAATSU training, is also appropriately determined according to the maximum pulse wave pressure. This allows effective and safe operation of the KAATSU training even when a user or a person who gives instructions of the KAATSU training to the user has little skill or experience. Moreover, the training apparatus according to the first invention determines the first reference pressure by using the pressure within the inflatable bag that has actually measured during the preprocessing. Accordingly, the first reference pressure is more likely to be proper than in the case where the first reference pressure is the one that has been previously determined on an empirical basis according to, for example, past data.

The first coefficient in the first invention is required to be set to a numeral equal to or larger than 0.2 but smaller than 1. Said control means may be adapted to set said first coefficient at a numeral that is not larger than 0.9. The reason of this lies in the fact that the pressure within the inflatable bag produced when the first coefficient is closer to 1 than 0.9 is appropriate for safe KAATSU training but slightly insufficient to achieve desired effects.

The first coefficient in the first invention can be determined at a numeral between 0.4 and 0.6, but not limited thereto. It has been found that a good balance between the safeness and the effect of the KAATSU training can be achieved more easily for most ordinary users when the KAATSU training is performed while applying the pressure around the first reference pressure determined by the first coefficient within this range, to the inflatable bag.

The first coefficient may either be fixed or variable. The training apparatus according to the first invention comprises means for entering information for specifying said first coefficient. Said control means may be adapted to determine said first coefficient by means of the information entered through said means for entering the information for specifying said first coefficient. The information entered in this case may be the first coefficient itself. Alternatively, it may be information for choosing either one of a plurality of first coefficients that have previously been prepared.

In the control means according to the first invention, said control means may be adapted to, upon said normal processing, control said pressure setting means so that said pressure setting means maintains the gas pressure within said inflatable bag at said the first reference pressure. This can further improve the safeness and effect of the KAATSU training.

The tight fitting band of the training apparatus according to the first invention may either be a single band or a plurality of bands.

When said tight fitting band includes a plurality of tight fitting bands, said pulse wave measuring means are equal in number to said tight fitting bands and are associated with respective one of said tight fitting bands. Moreover, said pulse wave measuring means may be adapted to measure said parameter that fluctuates along with the fluctuation of the magnitude of the pulse wave at a position near a predetermined region of muscles or a position closer to the distal end of the limb than the predetermined region of muscles around which the respective tight fitting bands are wrapped that are associated with the pulse wave measuring means, to generate a pulse wave data about the parameter. The pressure setting means in this case are equal in number to said tight fitting bands and are associated with respective one of said tight fitting bands. Moreover, said control means may be adapted to control, upon said preprocessing, said pressure setting means to determine the pulse wave component at the time point at which said maximum pulse wave pressure is produced and said first reference pressure for each of the limbs, said control means being adapted to control, upon said normal processing, each of said pressure setting means that are associated with said tight fitting bands, respectively, for compressing the respective limbs, in such a manner that the gas pressure within said inflatable bag of the tight fitting band associated with the pressure setting means falls within a predetermined range above or below said first reference pressure that is determined for the limb for which the associated tight fitting band is to be used.

The maximum pulse wave pressure that is determined for each tight fitting band in this case may be different from tight fitting band to tight fitting band. Such a training apparatus permits independent control of the compression pressures to be applied to the limbs by the tight fitting bands, respectively.

Effects similar to those obtained with the training apparatus according to the first invention can be achieved by using, for example, a following control segment for training.

A control segment for training according to the first invention is a control segment for training which constitutes a training apparatus when in combination with a tight fitting band including a belt having the length that is enough to be wrapped around a predetermined region of muscles of one of the limbs; fastening means for fastening said belt with said belt being wrapped around said predetermined region of muscles; and an inflatable bag provided in or on said belt, said inflatable bag being adapted to apply a predetermined compression pressure to said predetermined region of muscles by means of filling said inflatable bag with a gas to compress said predetermined region of muscles while said belt that has been wrapped around said predetermined region of muscles is fastened by said fastening means.

This control segment for training comprises pressure setting means that is capable of setting a gas pressure within said inflatable bag at a predetermined pressure; control means for controlling said pressure setting means in order to change said compression pressure; and pulse wave measuring means for measuring a predetermined parameter at a position near said predetermined region of muscles or a position closer to the distal end of the limb than said predetermined region of muscles, to generate a pulse wave data about the parameter, the parameter fluctuating along with the fluctuation of the magnitude of an arterial pulse wave that is changed in response to said compression pressure.

Then, said control means is adapted to direct said pressure setting means to perform preprocessing and normal processing. Said control means is also adapted to, upon said preprocessing, control said pressure setting means so that said pressure setting means changes the gas pressure within said inflatable bag; determine a pulse wave component at a time point at which the maximum pulse wave pressure is produced after receiving a plurality of said pulse wave data from said pulse wave measuring means during the time period when the pressure within said inflatable bag is changing, the maximum pulse wave pressure being the gas pressure within said inflatable bag at a time point at which the amplitude of the pulse wave component reaches the maximum; and determine a first reference pressure which is the pressure within the inflatable bag at a time point when such a pulse wave component is produced that has an amplitude obtained by means of multiplying the amplitude of the pulse wave component at the time point at which said maximum pulse wave pressure is produced with a predetermined first coefficient that is equal to or larger than 0.2 but smaller than 1, the first reference pressure being larger than the pressure within said inflatable bag at the time point at which said maximum pulse wave pressure is produced. Furthermore, said control means is adapted to, upon said normal processing, control said pressure setting means so that said pressure setting means keeps the gas pressure within said inflatable bag in a predetermined range above or below said the first reference pressure.

Effects similar to those obtained with the training apparatus according to the first invention can be achieved by using, for example, a following method.

A method according to the first invention is a method to be carried out in a control segment for training which constitutes a training apparatus when in combination with a tight fitting band including a belt having the length that is enough to be wrapped around a predetermined region of muscles of one of the limbs; fastening means for fastening said belt with said belt being wrapped around said predetermined region of muscles; and an inflatable bag provided in or on said belt, said inflatable bag being adapted to apply a predetermined compression pressure to said predetermined region of muscles by means of filling said inflatable bag with a gas to compress said predetermined region of muscles while said belt that has been wrapped around said predetermined region of muscles is fastened by said fastening means, the control segment comprising pressure setting means that is capable of setting a gas pressure within said inflatable bag at a predetermined pressure; control means for controlling said pressure setting means in order to change said compression pressure; and pulse wave measuring means for measuring a predetermined parameter at a position near said predetermined region of muscles or a position closer to the distal end of the limb than said predetermined region of muscles, to generate a pulse wave data about the parameter, the parameter fluctuating along with the fluctuation of the magnitude of an arterial pulse wave that is changed in response to said compression pressure.

In this method, said control means directs said pressure setting means to perform preprocessing and normal processing; upon said preprocessing, controls said pressure setting means so that said pressure setting means changes the gas pressure within said inflatable bag, and determines the maximum pulse wave pressure after receiving a plurality of said pulse wave data from said pulse wave measuring means during the time period when the pressure within said inflatable bag is changing, the maximum pulse wave pressure being the gas pressure within said inflatable bag at a time point at which the amplitude of the pulse wave component reaches the maximum; determines a first reference pressure which is the pressure within the inflatable bag at a time point when such a pulse wave component is produced that has an amplitude obtained by means of multiplying the amplitude of the pulse wave component at the time point at which said maximum pulse wave pressure is produced with a predetermined first coefficient that is equal to or larger than 0.2 but smaller than 1, the first reference pressure being larger than the pressure within said inflatable bag at the time point at which said maximum pulse wave pressure is produced; and upon said normal processing, controls said pressure setting means so that said pressure setting means keeps the gas pressure within said inflatable bag in a predetermined range above or below said the first reference pressure.

The second invention in this application is a training apparatus comprising a tight fitting band including a belt having the length that is enough to be wrapped around a predetermined region of muscles of one of the limbs; fastening means for fastening said belt with said belt being wrapped around said predetermined region of muscles; and an inflatable bag provided in or on said belt, said inflatable bag being adapted to apply a predetermined compression pressure to said predetermined region of muscles by means of filling said inflatable bag with a gas to compress said predetermined region of muscles while said belt that has been wrapped around said predetermined region of muscles is fastened by said fastening means; pressure setting means that is capable of setting a gas pressure within said inflatable bag at a predetermined pressure; control means for controlling said pressure setting means in order to change said compression pressure; and pulse wave measuring means for measuring a predetermined parameter at a position near said predetermined region of muscles or a position closer to the distal end of the limb than said predetermined region of muscles, to generate a pulse wave data about the parameter, the parameter fluctuating along with the fluctuation of the magnitude of an arterial pulse wave that is changed in response to said compression pressure.

Said control means in this training apparatus is adapted to direct said pressure setting means to perform preprocessing and normal processing. Said control means is also adapted to, upon said preprocessing, control said pressure setting means so that said pressure setting means changes the gas pressure within said inflatable bag; determine a pulse wave component at a time point at which the maximum pulse wave pressure is produced after receiving a plurality of said pulse wave data from said pulse wave measuring means during the time period when the pressure within said inflatable bag is changing, the maximum pulse wave pressure being the gas pressure within said inflatable bag at a time point at which the amplitude of the pulse wave component reaches the maximum; and determine a first reference pressure which is the pressure within the inflatable bag at a time point when such a pulse wave component is produced that has an amplitude obtained by means of multiplying the amplitude of the pulse wave component at the time point at which said maximum pulse wave pressure is produced with a predetermined first coefficient that is equal to or larger than 0.2 but smaller than 1, and a second reference pressure which is the pressure within the inflatable bag at a time point when such a pulse wave component is produced that has an amplitude obtained by means of multiplying the amplitude of the pulse wave component at the time point at which said maximum pulse wave pressure is produced with a predetermined second coefficient that is equal to or larger than 0.2 and larger than said first coefficient, the first reference pressure being larger than the pressure within said inflatable bag at the time point at which said maximum pulse wave pressure is produced, the second reference pressure being larger than the pressure within said inflatable bag at the time point at which said maximum pulse wave pressure is produced. Said control means is adapted to, upon said normal processing, control said pressure setting means so that said pressure setting means keeps the gas pressure within said inflatable bag in a predetermined range from said the first reference pressure to said the second reference pressure.

In the second invention, the second reference pressure is determined in a similar manner to the one used to obtain the first reference pressure, besides determining the first reference pressure as in the case of the first invention. The second coefficient for determining the second reference pressure is larger than the first coefficient. As a result, the pulse wave component produced when the second reference pressure is determined is larger than the pulse wave component produced when the first reference pressure is determined. This suggests that more blood is flowing through arteries or arteries force the blood stronger in the case where the pressure within the inflatable bag is equal to the second reference pressure than in the case where the pressure within the inflatable bag is equal to the first reference pressure, indicating that the second reference pressure is lower than the first reference pressure.

The training apparatus according to the second invention contributes to improve the safeness and effect of the KAATSU training by means of keeping the pressure within the inflatable bag in a range between the first reference pressure and the second reference pressure. In addition, when the first and second coefficients are appropriately determined, then the first and second reference pressures, which serve as reference pressures within the inflatable bag during the KAATSU training, are also appropriately determined according to the maximum pulse wave pressure. This allows effective and safe operation of the KAATSU training even when a user or a person who gives instructions of the KAATSU training to the user has little skill or experience.

Said control means in the second invention is adapted to set said second coefficient at a numeral that is not larger than 0.9. The reason of this lies in the fact that the pressure within the inflatable bag around the second coefficient, if produced when the second coefficient is determined to be closer to 1 than 0.9, is appropriate for safe KAATSU training but slightly insufficient to achieve desired effects.

Said control means in the second invention may be adapted to set said second coefficient at a numeral between 0.5 and 0.7. It has been found that the second reference pressure determined by the second coefficient would be an appropriate lower limit pressure for effective and safe operations of the KAATSU training for many users.

The second coefficient may either be fixed or variable. The training apparatus according to the second invention comprises means for entering information for specifying said second coefficient. Said control means may be adapted to determine said second coefficient by means of the information entered through said means for entering the information for specifying said second coefficient. The information entered in this case may be the second coefficient itself. Alternatively, it may be information for choosing either one of a plurality of second coefficients that have previously been prepared.

As in the case of the first invention, said control means may be adapted to set said first coefficient at a numeral between 0.4 and 0.6. It has been found that the first reference pressure determined by the first coefficient would be an appropriate upper limit pressure for effective and safe operations of the KAATSU training for many users.

As in the case of the first invention, the first coefficient may either be fixed or variable. The training apparatus in the second invention comprises means for entering information for specifying said first coefficient, and said control means may be adapted to determine said first coefficient by means of the information entered through said means for entering the information for specifying said first coefficient. The information entered in this case may be the first coefficient itself. Alternatively, it may be information for choosing either one of a plurality of first coefficients that have previously been prepared.

The training apparatus of the second invention comprises means for entering information for specifying an in-between numeral which is a numeral not smaller than said first coefficient and not larger than said second coefficient, and said control means may be adapted to determine both said first coefficient and said second coefficient according to one information entered through said means for entering the information for specifying said in-between numeral. With such a training apparatus, it is convenient in that the user of the training apparatus can leave determination of the first and second coefficient to the training apparatus after he or she enters a single in-between numeral.

The control means can determine the first and second coefficients from the in-between numeral by means of any one of appropriate approaches. For example, said control means of such a training apparatus may use results obtained by subtracting and adding a predetermined numeral that is smaller than 1 from and to the numeral that is specified by one information entered through said means for entering the information for specifying said in-between numeral, as the first coefficient and the second coefficient, respectively, or may use results obtained through multiplying the numeral that is specified by one information entered through said means for entering the information for specifying said in-between numeral with a predetermined numeral that is smaller than 1 and a predetermined numeral that is larger than 1, as the first coefficient and the second coefficient, respectively.

The tight fitting band of the training apparatus according to the second invention may either be a single band or a plurality of bands.

When the tight fitting band includes a plurality of tight fitting bands, said pulse wave measuring means are equal in number to said tight fitting bands and are associated with respective one of said tight fitting bands. Moreover, said pulse wave measuring means may be adapted to measure a predetermined parameter that fluctuates along with the fluctuation of the magnitude of the pulse wave at a position near a predetermined region of muscles or a position closer to the distal end of the limb than the predetermined region of muscles around which the respective tight fitting bands are wrapped that are associated with the pulse wave measuring means, to generate a pulse wave data about the parameter. In addition, said pressure setting means in this case are equal in number to said tight fitting bands and are associated with respective one of said tight fitting bands. Moreover, said control means may be adapted to control, upon said preprocessing, said pressure setting means to determine the pulse wave component at the time point at which said maximum pulse wave pressure is produced, said first reference pressure, and said second reference pressure, for each of the limbs, said control means being adapted to control, upon said normal processing, each of said pressure setting means that are associated with said tight fitting bands, respectively, for compressing the respective limbs, in such a manner that the gas pressure within said inflatable bag of the tight fitting band associated with the pressure setting means falls within a predetermined range between said first reference pressure and said second reference pressure that are determined for the limb for which the associated tight fitting band is to be used.

The maximum pulse wave pressure that is determined for each tight fitting band in this case may be different from tight fitting band to tight fitting band. Such a training apparatus permits independent control of the compression pressures to be applied to the limbs by the tight fitting bands, respectively.

Effects similar to those obtained with the training apparatus according to the second invention can be achieved by using, for example, a following control segment for training.

A control segment for training according to the second invention is a control segment for training which constitutes a training apparatus when in combination with a tight fitting band including a belt having the length that is enough to be wrapped around a predetermined region of muscles of one of the limbs; fastening means for fastening said belt with said belt being wrapped around said predetermined region of muscles; and an inflatable bag provided in or on said belt, said inflatable bag being adapted to apply a predetermined compression pressure to said predetermined region of muscles by means of filling said inflatable bag with a gas to compress said predetermined region of muscles while said belt that has been wrapped around said predetermined region of muscles is fastened by said fastening means.

This control segment for training comprises pressure setting means that is capable of setting a gas pressure within said inflatable bag at a predetermined pressure; control means for controlling said pressure setting means in order to change said compression pressure; and pulse wave measuring means for measuring a predetermined parameter at a position near said predetermined region of muscles or a position closer to the distal end of the limb than said predetermined region of muscles, to generate a pulse wave data about the parameter, the parameter fluctuating along with the fluctuation of the magnitude of an arterial pulse wave that is changed in response to said compression pressure.

Then said control means of this control segment for training is adapted to direct said pressure setting means to perform preprocessing and normal processing. Said control means is also adapted to, upon said preprocessing, control said pressure setting means so that said pressure setting means changes the gas pressure within said inflatable bag; determine a pulse wave component at a time point at which the maximum pulse wave pressure is produced after receiving a plurality of said pulse wave data from said pulse wave measuring means during the time period when the pressure within said inflatable bag is changing, the maximum pulse wave pressure being the gas pressure within said inflatable bag at a time point at which the amplitude of the pulse wave component reaches the maximum; and determine a first reference pressure which is the pressure within the inflatable bag at a time point when such a pulse wave component is produced that has an amplitude obtained by means of multiplying the amplitude of the pulse wave component at the time point at which said maximum pulse wave pressure is produced with a predetermined first coefficient that is equal to or larger than 0.2 but smaller than 1, and a second reference pressure which is the pressure within the inflatable bag at a time point when such a pulse wave component is produced that has an amplitude obtained by means of multiplying the amplitude of the pulse wave component at the time point at which said maximum pulse wave pressure is produced with a predetermined second coefficient that is equal to or larger than 0.2 and larger than said first coefficient, the first reference pressure being larger than the pressure within said inflatable bag at the time point at which said maximum pulse wave pressure is produced, the second reference pressure being larger than the pressure within said inflatable bag at the time point at which said maximum pulse wave pressure is produced. Furthermore, said control means is adapted to, upon said normal processing, control said pressure setting means so that said pressure setting means keeps the gas pressure within said inflatable bag in a predetermined range from said the first reference pressure to said the second reference pressure.

Effects similar to those obtained with the training apparatus according to the second invention can be achieved by using, for example, a following method.

A method of the second invention is a method to be carried out in a control segment for training which constitutes a training apparatus when in combination with a tight fitting band including a belt having the length that is enough to be wrapped around a predetermined region of muscles of one of the limbs; fastening means for fastening said belt with said belt being wrapped around said predetermined region of muscles; and an inflatable bag provided in or on said belt, said inflatable bag being adapted to apply a predetermined compression pressure to said predetermined region of muscles by means of filling said inflatable bag with a gas to compress said predetermined region of muscles while said belt that has been wrapped around said predetermined region of muscles is fastened by said fastening means, the control segment comprising: pressure setting means that is capable of setting a gas pressure within said inflatable bag at a predetermined pressure; control means for controlling said pressure setting means in order to change said compression pressure; and pulse wave measuring means for measuring a predetermined parameter at a position near said predetermined region of muscles or a position closer to the distal end of the limb than said predetermined region of muscles, to generate a pulse wave data about the parameter, the parameter fluctuating along with the fluctuation of the magnitude of an arterial pulse wave that is changed in response to said compression pressure.

In this method, said control means directs said pressure setting means to perform preprocessing and normal processing; upon said preprocessing, controls said pressure setting means so that said pressure setting means changes the gas pressure within said inflatable bag; determines a pulse wave component at a time point at which the maximum pulse wave pressure is produced after receiving a plurality of said pulse wave data from said pulse wave measuring means during the time period when the pressure within said inflatable bag is changing, the maximum pulse wave pressure being the gas pressure within said inflatable bag at a time point at which the amplitude of the pulse wave component reaches the maximum; and determine a first reference pressure which is the pressure within the inflatable bag at a time point when such a pulse wave component is produced that has an amplitude obtained by means of multiplying the amplitude of the pulse wave component at the time point at which said maximum pulse wave pressure is produced with a predetermined first coefficient that is equal to or larger than 0.2 but smaller than 1, and a second reference pressure which is the pressure within the inflatable bag at a time point when such a pulse wave component is produced that has an amplitude obtained by means of multiplying the amplitude of the pulse wave component at the time point at which said maximum pulse wave pressure is produced with a predetermined second coefficient that is equal to or larger than 0.2 and larger than said first coefficient, the first reference pressure being larger than the pressure within said inflatable bag at the time point at which said maximum pulse wave pressure is produced, the second reference pressure being larger than the pressure within said inflatable bag at the time point at which said maximum pulse wave pressure is produced; and upon said normal processing, controls said pressure setting means so that said pressure setting means keeps the gas pressure within said inflatable bag in a predetermined range from said the first reference pressure to said the second reference pressure.

The following description can apply to both the first and second inventions.

Both in the first and second inventions, as described above, the control means controls said pressure setting means so that said pressure setting means changes the gas pressure within said inflatable bag. The change in gas pressure within the inflatable bag may be either continuous or stepwise. The term "stepwise" as used herein means that there are time intervals during which the pressure does not change over time. In addition, the gas pressure within the inflatable bag may be either increased or decreased over time. Finally, it is only required that the gas pressure within the inflatable bag is changed so that the maximum pulse wave pressure (more exactly, the maximum pulse wave pressure and the first reference pressure in the case of the first invention, and the second reference pressure in addition to them in the case of the second invention) can be determined.

As described above, the maximum pulse wave pressure is determined according to the pulse wave data. There is no limitation about how it is determined according to the pulse wave data. A plurality of pulse wave data are sent from the pulse wave measuring means to the control means in a continuous manner for example. The pulse wave data that are continuously dispatched from the pulse wave measuring means may be sent to the control means without any interruption, or alternatively, they may be sent to the control means with certain or predetermined time intervals.

When the control means control, upon said preprocessing, said pressure setting means in such a manner that said pressure setting means increases the pressure within said inflatable bag to a level that is higher than a pressure expected to exceed the first reference pressure, and then reduces the pressure within said inflatable bag, the control means may determine the maximum pulse wave pressure in the following manner.

For example, said control means may be adapted to continuously receive said pulse wave data from said pulse wave measuring means during the time period when the pressure within said inflatable bag is decreasing in said preprocessing, and determine a pulse wave component at the time point at which the maximum pulse wave pressure is produced when the pulse wave component reaches the maximum, from the previous (or previous and following as the case may be) pulse wave data, when said pulse wave data indicates that said magnitude of the pulse wave component becomes smaller than the previous one.

According to the studies made by the present inventor, it has been found that the pulse wave components gradually become larger as the pressure to compress the proximal portion of the limb is reduced, and then gradually become smaller after the pressure becomes lower than a certain pressure. Thus, the pulse wave components become larger when the pressure applied to compress the proximal portion of the limb is reduced, and when the pulse wave components turn to become smaller, then the maximum pulse wave component can be found slightly before the turning point where the pulse wave components begin to decrease. In the aforementioned procedure, the maximum pulse wave component corresponding to the maximum pulse wave pressure is determined or expected from the previous pulse wave data (or the preceding and following pulse wave data) when said pulse wave data indicates that said magnitude of the pulse wave component becomes smaller than the previous one.

In addition, said control means may be adapted to continuously receive said pulse wave data from said pulse wave measuring means during the time period when the pressure within said inflatable bag is decreasing in said preprocessing, and determine, as the maximum pulse wave pressure, an immediately preceding gas pressure within said inflatable bag when said pulse wave data indicates that said magnitude of the pulse wave component becomes smaller than the previous one. This approach also makes good use of the nature of the pulse wave in which the pulse wave components gradually become larger as the pressure to compress the proximal portion of the limb is reduced, and then gradually become smaller after the pressure becomes lower than a certain pressure. When this approach is used, it is better that the pulse wave data be sent to the control means in a continuous manner, if possible, or within as short period of time as possible.

In the aforementioned two cases, it is necessary that the gas pressure within the inflatable bag is increased to a level higher than a pressure that is expected to be the first reference pressure, and the gas pressure within the inflatable bag is reduced therefrom. The pressure that is expected to be the first reference pressure is different from user to user. However, it is possible to empirically expect a possible range within which it falls, so that this can substantially be done without any trouble. More specifically, the should-be-increased gas pressure within the inflatable bag is about 230 to 250 mmHg on average. The training apparatuses of the first and second inventions may be adapted to allow the should-be-increased gas pressure within the inflatable bag, which should be higher than the first reference pressure, to be entered through the input means before the preprocessing for determining the pulse wave component at the time point at which the maximum pulse wave pressure is produced, and to allow the control means receiving the input from the input means to direct the pressure setting means to rise the gas pressure within the inflatable bag to a pressure based on that input.

Said control means may be adapted to, upon said preprocessing, control said pressure setting means in such a manner that said pressure setting means reduces the pressure within said inflatable bag to a level that is lower than a pressure expected to be lower than the maximum pulse wave pressure, and then increases the pressure within said inflatable bag. Unlike to the aforementioned case, the maximum pulse wave pressure etc. are determined while the pressure within the inflatable bag is increased.

In this case, said control means may be adapted to continuously receive said pulse wave data from said pulse wave measuring means during the time period when the pressure within said inflatable bag is increasing in said preprocessing, and determine a pulse wave component at the time point at which the maximum pulse wave pressure is produced when the pulse wave component reaches the maximum, from the previous pulse wave data, when said pulse wave data indicates that said magnitude of the pulse wave component becomes smaller than the previous one. In addition, said control means may be adapted to continuously receive said pulse wave data from said pulse wave measuring means during the time period when the pressure within said inflatable bag is increasing in said preprocessing, and determine, as the maximum pulse wave pressure, an immediately preceding gas pressure within said inflatable bag when said pulse wave data indicates that said magnitude of the pulse wave component becomes smaller than the previous one.

According to the studies made by the present inventor, it has been found that the pulse wave components gradually become larger as the pressure to compress the proximal portion of the limb is increased, and then gradually become smaller after the pressure becomes higher than a certain pressure. Thus, with these two approaches, as in the case where the pressure to compress the proximal portion of the limb is reduced, it is possible to determine the pulse wave component at the time point at which the maximum pulse wave pressure is produced. When these two approaches are used, it is necessary that the gas pressure within the inflatable bag is kept lower than the pressure expected to be the maximum pulse wave pressure, and that the gas pressure within the inflatable bag is increased therefrom. This can be achieved by means of, for example, the gas pressure within the inflatable bag from the ordinary pressure.

The parameter that fluctuates along with the fluctuation of the magnitude of the arterial pulse wave which the pulse wave measuring means measures may be a parameter associated with any one of physical quantities as long as it is associated with the magnitude of the pulse wave. The pulse wave measuring means may be a sensor for measuring a surface pressure from the skin where it contacts. It may be a sensor for measuring a surface pressure from the skin that fluctuates along with the pulse wave. The pulse wave appears as pulsation on the skin, so that the aforementioned pulse wave measuring means measures, as the parameter, the surface pressure from the skin that fluctuates along with the pulsation.

Alternatively, the pulse wave measuring means may be adapted to measure the gas pressure within said inflatable bag as said parameter. As described above, the pulse wave appears as pulsation on the skin. This pulsation causes the change in air pressure within the inflatable bag of the tight fitting band which has been wrapped around the proximal portion of the limb. The aforementioned pulse wave measuring means measures this gas pressure within the inflatable bag as the parameter.

It is noted that the pulse wave measuring means is only required to measure the pulse wave near said predetermined region of muscles or a position closer to the distal end of the limb than said predetermined region of muscles. When the pulse wave measuring means measures the pulse wave near the predetermined region of the muscles, the pulse wave measuring means does not necessarily measure the pulse wave at a position closer to the distal end of the limb than the predetermined region.

MODES FOR CARRYING OUT THE INVENTION

Figure 1:
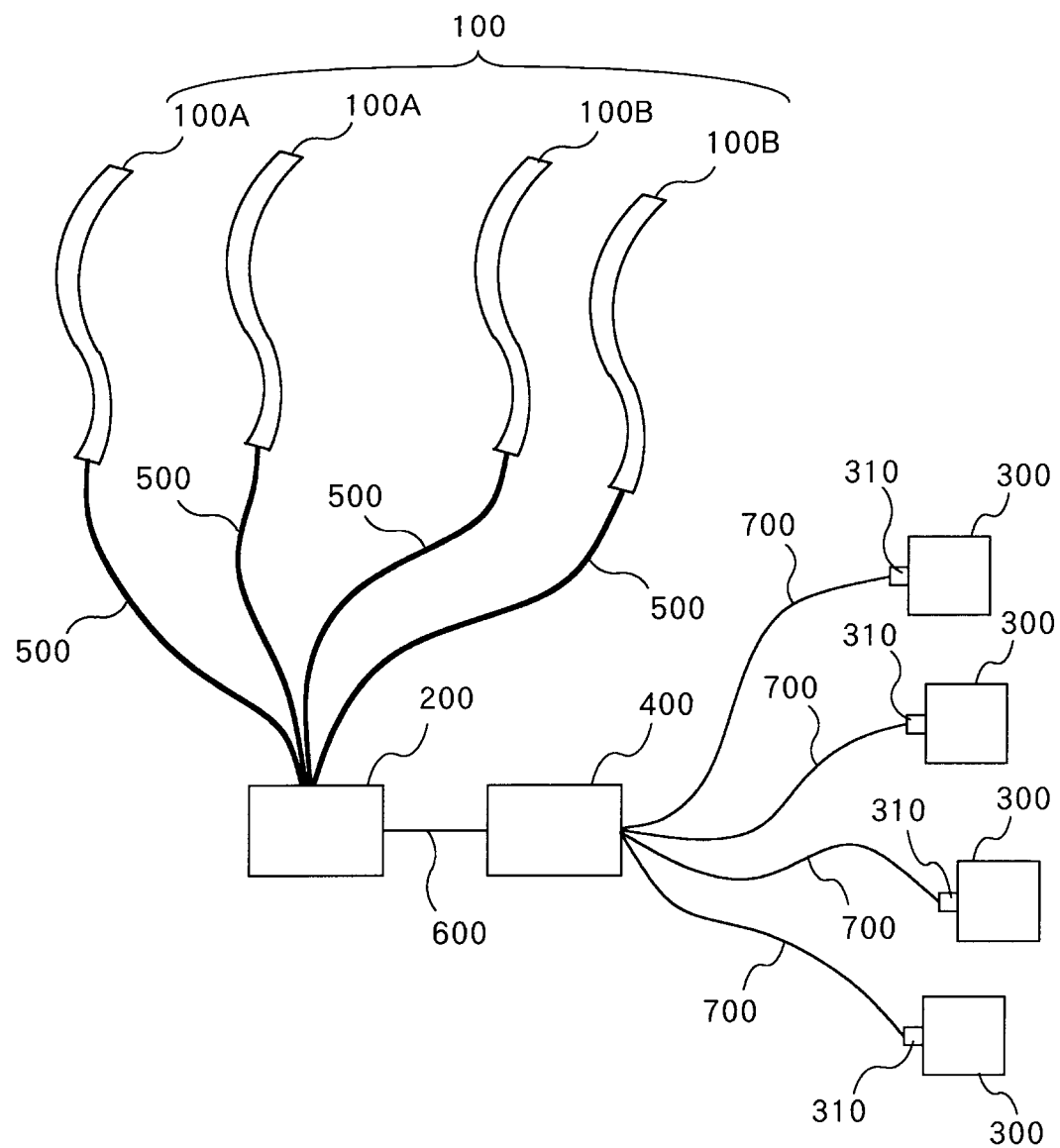
FIG. 1 is a view schematically showing the entire configuration of a training apparatus according to a first embodiment of the present invention.

Preferred first and second embodiments of the present invention are described now with reference to the drawing, in which like numerals designate similar parts throughout the figures in both embodiments and some redundant descriptions will be omitted as the case may be.

First Embodiment

FIG. 1 is a view schematically showing the entire configuration of a training apparatus according to an embodiment of the present invention.

As shown in FIG. 1, the training apparatus according to this embodiment comprises a tight fitting band 100, a main device 200, a measuring segment 300, and a control segment 400. In this embodiment, although the main device 200 is described as a separate component from the control segment 400, they can be integrated to each other as a single component.

Figure 2:
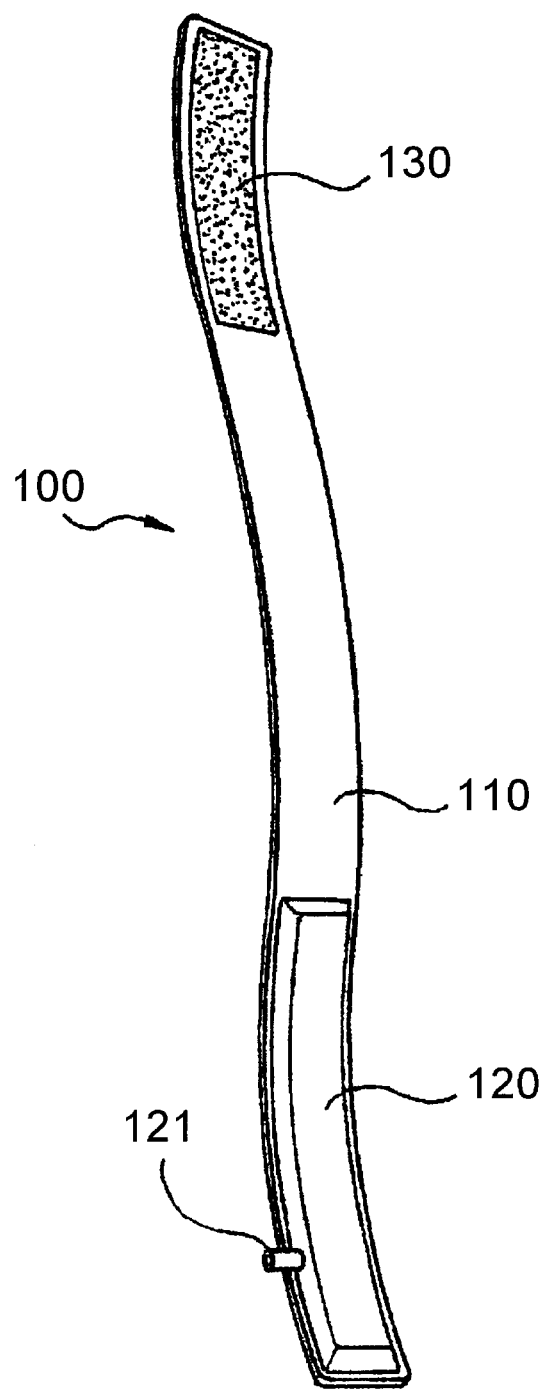
FIG. 2 is a perspective view showing a tight fitting band included in the training apparatus in FIG. 1.
Figure 3:
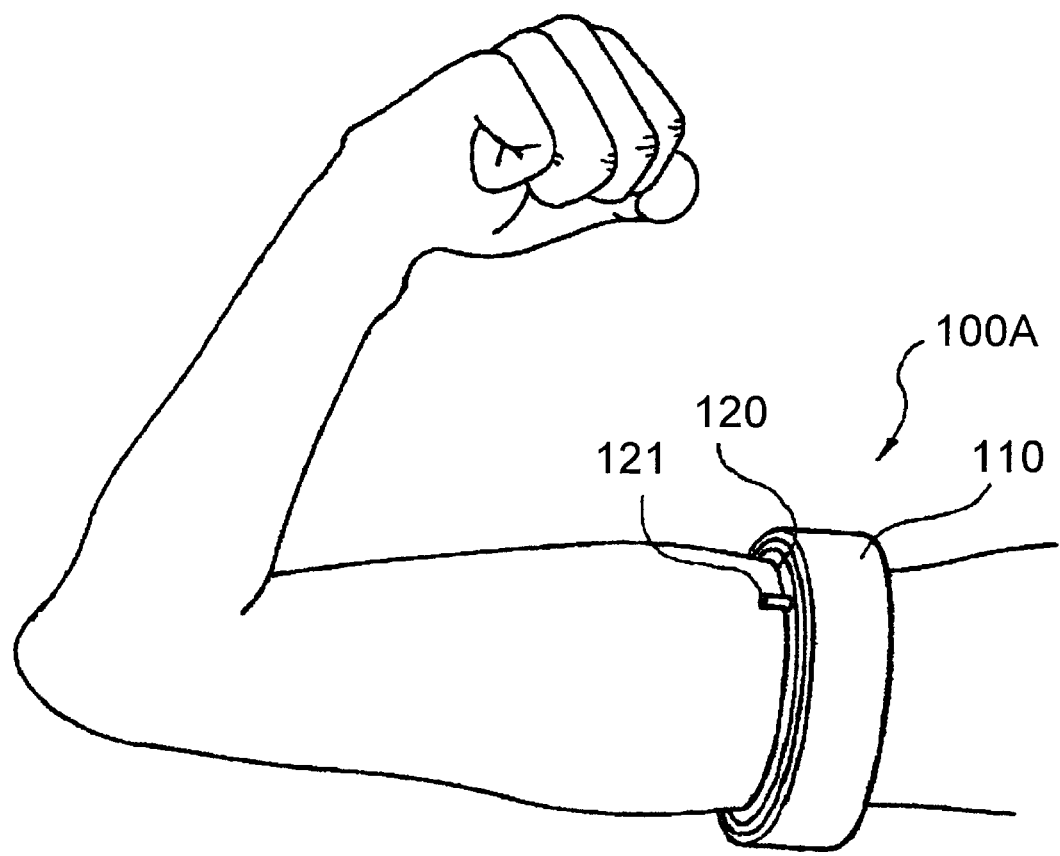
FIG. 3 is a view illustrating how the tight fitting band for arms included in the training apparatus in FIG. 1 is used.
Figure 4:
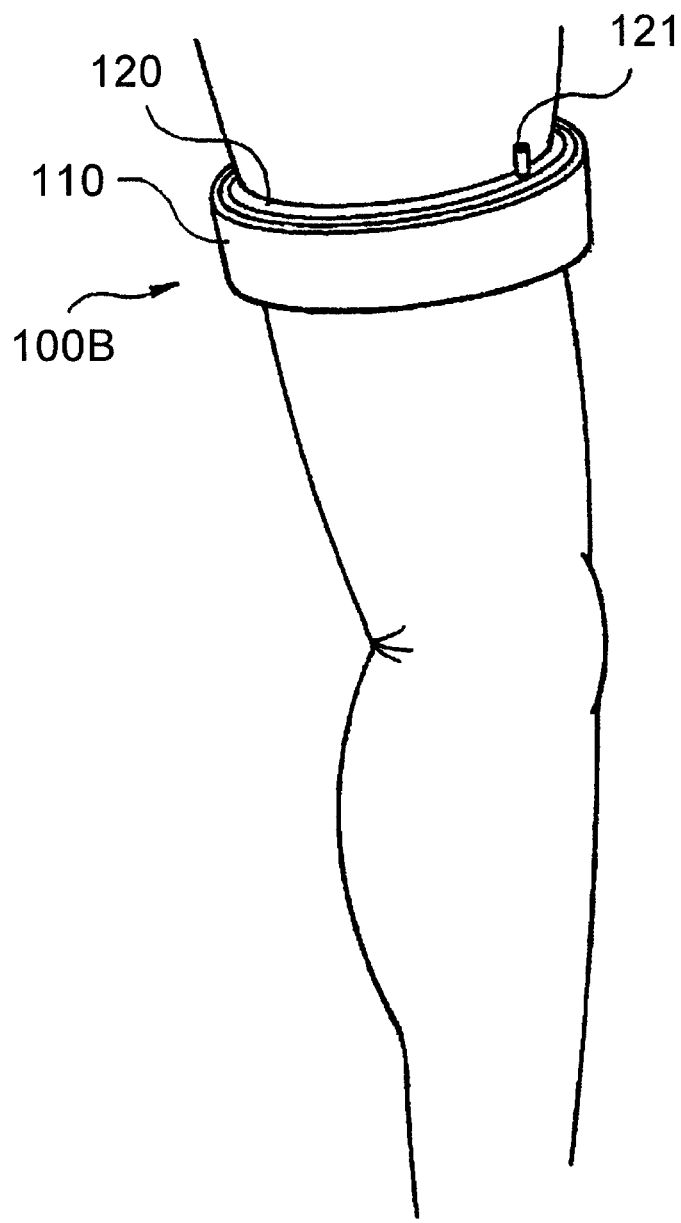
FIG. 4 is a view illustrating how the tight fitting band for legs included in the training apparatus in FIG. 1 is used.

The tight fitting band 100 in this embodiment is configured as shown in FIGS. 2, 3, and 4. FIG. 2 is a perspective view showing an embodiment of the tight fitting band 100. FIGS. 3 and 4 are views illustrating how the tight fitting device 100 is used.

The tight fitting band 100 in this embodiment comprises a plurality of, more specifically, four members as shown in FIG. 1. The reason why there are four tight fitting bands 100 is to allow compression of the arms and legs of a user who receives KAATSU training. Of the tight fitting bands 100 in this embodiment, tight fitting bands 100A are for arms (each of which is intended to be wrapped around an arm for the compression of the arm) while tight fitting bands 100B are for legs (each of which is intended to be wrapped around a leg for the compression of the leg). The number of the tight fitting bands 100 is not necessarily four. Any number equal to or larger than one may be used. The number of the tight fitting bands 100A for arms is not necessarily identical to the number of the tight fitting bands 100B for legs. More than four tight fitting bands may be provided to cope with cases where two or more persons perform the KAATSU training at the same time.

Each tight fitting band 100 in this embodiment is intended to be wrapped around the proximal part of one of the limbs to apply a predetermined compression pressure to the proximal part of the limb. The tight fitting band 100 is adapted to modulate the pressure to be applied to the proximal part of the limb in order to compress the proximal part of the limb. This tight fitting band 100 basically comprises a belt 110, an inflatable tube 120, and a fastening member 130, in this embodiment.

Details of the belt 110 do not matter as long as it can be wrapped around the proximal part of the limb (more specifically, an appropriate position near the top of the arm or near the top of the leg that is suitable for the restriction of the blood flow by the external compression; hereinafter, which may also be referred herein to as a "compression target range") around which the tight fitting band 100 is to be wrapped.

The belt 110 in this embodiment may be made of a material having a certain degree of stretchability, but not limited thereto. For example, the belt 110 is made of polyurethane.

The length of the belt 110 according to this embodiment may be determined based on the girth of the compression target range of a user. The length of the belt 110 may be any length that is longer than the girth of the compression target range. The length of the belt 110 in this embodiment is twice or longer than the girth of the compression target range. The length of the belt 110 of the tight fitting band 100A for arms according to this embodiment is determined in view of the girth of the compression target range on the arm being 26 cm. More specifically it is 90 cm. The length of the belt 110 of the tight fitting band 100B for legs is determined in view of the girth of the compression target range on the leg being 45 cm. More specifically, it is 145 cm.

The width of the belt 110 according to this embodiment may suitably be determined for the respective ranges to be compressed by the tight fitting band 100. For example, the belt 110 of the tight fitting band 110A for arms, of which compression target range is on the proximal part of an arm, may have a width of approximately 3 cm. The belt 110 of the tight fitting band 110B for legs, of which compression target range is on the proximal part of a leg, may have a width of approximately 5 cm. It is preferable that each belt 110 be narrow enough to prevent it from being positioned over the muscle belly even when the arm or leg compressed by it is bent.

The inflatable bag 120 is attached to the belt 110. The inflatable bag 120 in this embodiment is attached to one surface of the belt 110. However, the way to attach the inflatable bag 120 to the belt 110 is not limited thereto. The inflatable bag 120 may be provided within a tube-shaped belt 110.

One end of the inflatable bag 120 is aligned with the corresponding end of the belt 110 (the lower end of the belt 110 in FIG. 2) but not limited thereto. The inflatable bag 120 is an air-tight bag. The inflatable bag 120 in this embodiment is made of a stretchable rubber similar to that of, for example, an inflatable bladder used in a blood pressure cuff. The material of the inflatable bag 120 is not limited thereto. Any material that can retain air tightness may appropriately be used.

The length of the inflatable bag 120 is, but not limited to, generally equal to the girth of the compression target range in this embodiment. The inflatable bag 120 of the tight fitting band 100A for arms is 25 cm in length while the inflatable bag 120 of the tight fitting band 100B for legs is 45 cm in length, in this embodiment.

In addition, the width of the inflatable bag 120 may suitably be determined for the respective ranges to be compressed by the tight fitting band 100. In this embodiment, the inflatable bag 120 of the tight fitting band 100A for arms is approximately 3 cm in width while the inflatable bag 120 of the tight fitting band 100B for legs is approximately 5 cm in width, both of which are not limited thereto.

The inflatable bag 120 has a connection port 121 that is communicated with the inside of the inflatable bag 120 in order to allow it to be connected with the main device 200 through, for example, a connecting pipe 500 comprised of a rubber tube. As will be described below, through the connection port 121, a gas (air in this embodiment) is introduced into the inflatable bag 120 or the gas in the inflatable bag 120 escapes therefrom to the outside.

The fastening member 130 is for fastening the belt 110 so that it is held with being wrapped around the compression target range. The fastening member 130 in this embodiment is a hook-and-loop fastener provided at the other end of the belt 110 (the upper end of the belt 110 in FIG. 2) on the side of the belt 110 where the inflatable bag 120 is provided. The fastening member 130 can be fastened to any part on the entire surface of the belt 110 where the inflatable bag 120 is not provided.

When inflatable bag 120 is filled with air with the belt 110 being wrapped around the compression target range and fastened by the fastening member 130, the tight fitting band 100 applies an appropriate pressure to the compression target range and compresses it. On the other hand, removal of the air from the inflatable bag 120 at that state results in a lower pressure being applied to the compression target range by the tight fitting band 100.

The main device 200 is designed to supply a gas to the inflatable bag 120 and remove the gas from the inflatable bag 120. Any one of possible configurations may be used for both mechanisms to supply a gas to the inflatable bag 120 and remove the gas from the inflatable bag 120.

Figure 5:
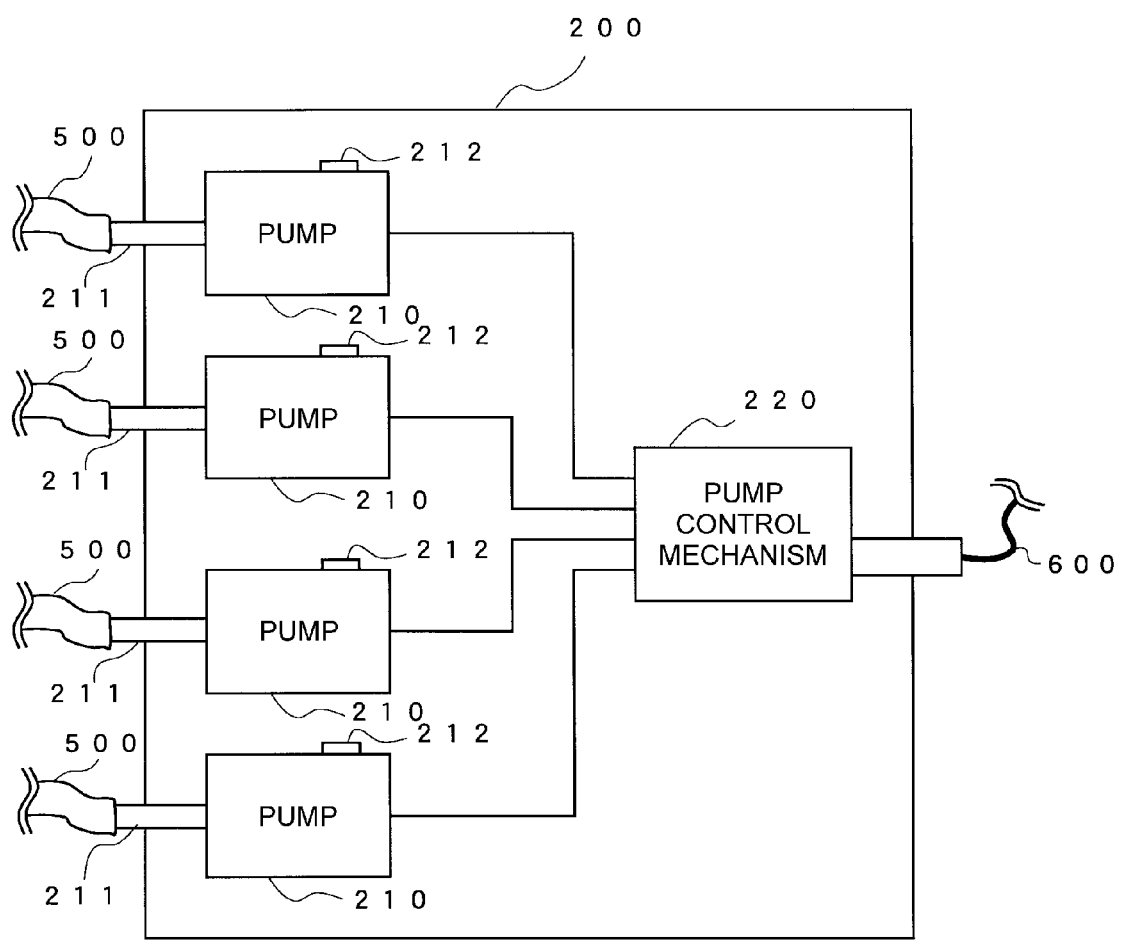
FIG. 5 is a view schematically showing an internal configuration of a main device included in the training apparatus in FIG. 1.

An illustrative configuration of the main device 200 is schematically shown in FIG. 5. As shown in FIG. 5, the main device 200 is composed of four pumps 210 and a pump control mechanism 220. These four pumps 210 are connected to four members of the tight fitting band 100, respectively, through the respective connecting pipes 500, and are associated with the corresponding tight fitting band 100 to which it is connected.

The pump 210 has a function of sucking the surrounding gas (air in this embodiment) and supplying it to the outside of a pump connection port 211 which will be described below. It includes a valve which is not shown. By opening the valve, the gas in the pump 210 can be discharged to the outside. Each of the four pumps 210 has its own pump connection port 211 and is connected to the inflatable bag 120 through the connecting pipe 500 connected thereto and the connection port 121. When the pump 210 forces the gas, the gas is introduced into the inflatable bag 120 of the corresponding tight fitting band 100 that is associated with that pump 210. When the pump 210 opens the valve, the gas can be removed from the inflatable bag 120 of the corresponding tight fitting band 100 that is associated with that pump 210.

As will be described below, the pump control mechanism 220 controls the pumps 210 according to the data from the control segment 400 to direct the pump(s) 210 to supply the gas into the inflatable bag 120 or remove the gas from the inflatable bag 120. In order to make it possible to receive the data in question, the main device 200 is connected to the control segment 400 via a cable 600 having one end connected to a terminal provided in or on the pump control mechanism 220.

Each pump 210 has a pressure sensor 212. The pressure sensor 212 is for measuring an air pressure within the pump 210. The air pressure within the pump 210 is equal to the air pressure within the inflatable bag 120. Accordingly, the pressure sensor 212 is for measuring the pressure within the inflatable bag 120. The pressure within the inflatable bag 120 that is detected by the pressure sensor 212 is supplied to the control segment 400 through the pump control mechanism 220 almost real time.

The measuring segment 300 is for measuring an arterial pulse wave in the limb that fluctuates due to the compression force, when the tight fitting band 100 is placed on a predetermined compression target range of the limb and the tight fitting band 100 compresses the compression target range of the limb, near or distal to the compression target range of the limb around which the tight fitting band 100 is wrapped.

The measuring segment 300 in this embodiment comprises four members, as in the case of the tight fitting band 100. The four measuring segments 300 are associated with one of the tight fitting bands 100. This means that the training apparatus in this embodiment includes four pairs of the tight fitting band 100 and the measuring segment 300.

The measuring segment 300 in this embodiment is designed to measure pulse waves as described above, and generate a pulse wave data representing the measured pulse wave. The pulse waves to be measured by using the measuring segment 300 may be either volume pulse waves or pressure pulse waves. Devices for measuring pulse waves themselves are well known in the art and an appropriate one of them may be used. The measuring segment 300 in this embodiment is the one that measures a pressure pulse wave as the pulse wave. The measuring segment 300 for measuring the pressure pulse waves in this embodiment is implemented by a pressure sensor capable of measuring a surface pressure. If a volume pulse wave is to be measured as the pulse wave, the measuring segment 300 may be achieved by using, for example, a phototransistor that is used in measuring photoelectric volume pulse waves. It is noted that the pulse wave may be measured based on the change in pressure within the inflatable bag 120 that is determined according to slight relaxation and contraction of blood vessels of the user obtained with the pressure sensor 212 provided in the pump 210.

The measuring segment 300 in this embodiment is capable of continuously measuring, without any interruption over time, a predetermined parameter that fluctuates according to the fluctuation in magnitude of the pulse wave, but not limited thereto. In other words, the measuring segment 300 is capable of continuously measuring a predetermined parameter that fluctuates according to the fluctuation in magnitude of the possibly ever-changing pulse wave. Alternatively, the measuring segment 300 may be adapted to measure a predetermined parameter that fluctuates according to the fluctuation in magnitude of the pulse wave at a predetermined time interval such as in every 30 seconds.

Each of the four measuring segments 300 measures the magnitude of the pulse wave components and generates the pulse wave data about the aforementioned parameter to send it to the control segment 400. In order to make it possible, the measuring segment 300 has an output terminal 310 (see FIG. 1), and is adapted to send the pulse wave data to the control segment 400 through a cable 700 having one end connected to the output terminal 310. The other end of the cable 700 is connected to the control segment 400. The mechanism for sending the pulse wave data to the control segment 400 is not limited thereto. Instead, data may be sent to the control segment 400 in a wireless manner by using, for example, light or radiowaves. In this embodiment, the pulse wave data generated by the measuring segment 300 according to the parameter measured continuously without any interruption, is sent to the control segment 400 almost real time.

The measuring segment 300 may be integrated with the tight fitting band 100 as a single unit, although this embodiment does not employ such a configuration.

The control segment 400 is for controlling the main device 200. More specifically, the control segment 400 generates data for controlling each of the four pumps 210 in the main device 200, and sends it to the pump control mechanism 220 to direct the pump control mechanism 220 to control the pumps 210.

In addition, the control segment 400 comprises an input device (not shown) provided outside thereof. The input device is a known input device including a numeric keypad. Information to be provided with the input device will be described below.

Figure 6:
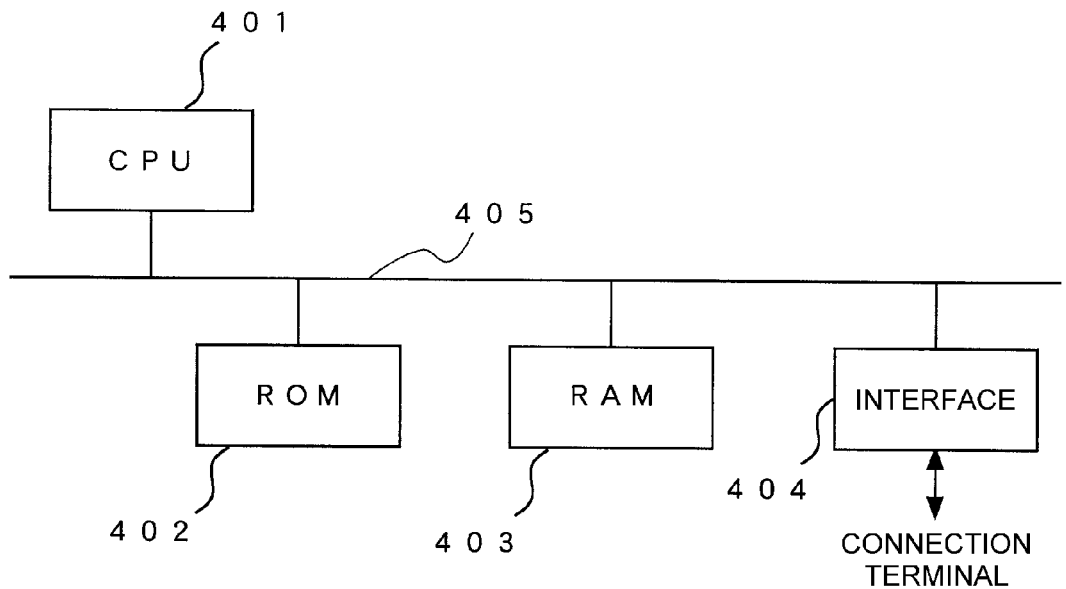
FIG. 6 is a hardware configuration of a control segment included in the training apparatus in FIG. 1.

An internal configuration of the control segment 400 is schematically shown in FIG. 6. The control segment 400 contains a computer wherein a CPU 401, an ROM 402, an RAM 403 and an interface 404 are connected to each other through a bus 405.

The CPU 401 is a central processing unit that controls the entire control segment 400. The ROM 402 records a program and data that are necessary for the processing described below to be carried out by the control segment 400. The CPU 401 executes the processing described below according to this program. The ROM 402 may be embodied by using a flash ROM. The RAM 403 is for providing a working area for the execution of the aforementioned program. The interface 404 is a device used to exchange data with the outside. In addition to the ROM 402 and the RAM 403, a hard disk having similar functions to those of them may be provided.

The interface 404 is connected to connection terminals (not shown) that can be connected to the other end of the cable 600, and four connection terminals (not shown) that can be connected to the other end of the cable 700. The aforementioned pulse wave data supplied from the measuring segment 300 is received by the interface 404 through the cable 700. In addition, control data described below is sent from the interface 404 to the main device 200 through the cable 600. In addition, the interface 404 receives, via the cable 600, the pressure within each pump 210 (the pressure within each inflatable bag 120 corresponding to the pump 210) at that time measured by the pressure sensor 212 provided in each pump 210 via the cable 600. The interface 404 is also connected to the aforementioned input device and receives the data generated as a result of the input device being used.

Figure 7:
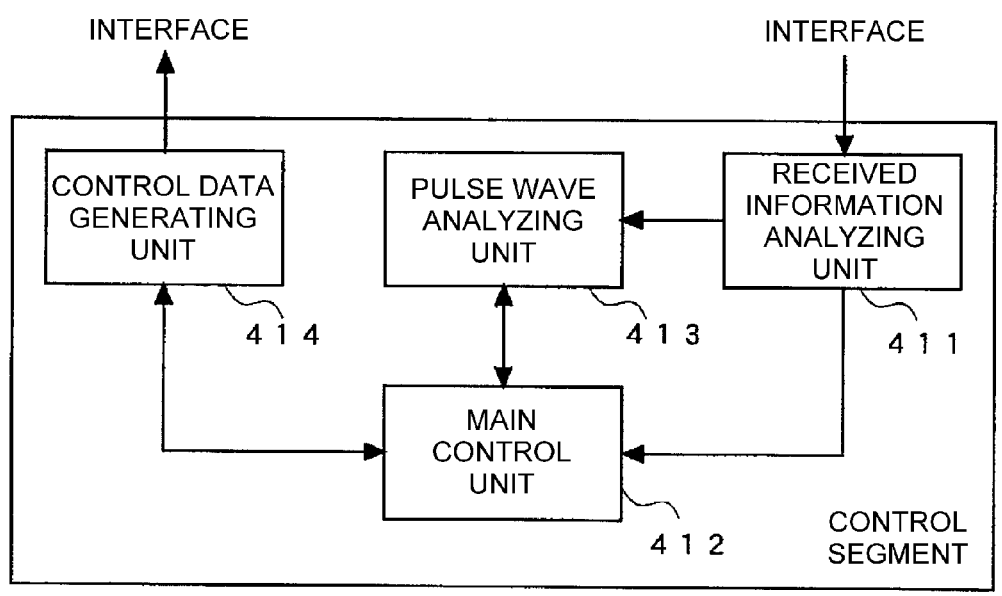
FIG. 7 is a view showing a functional block generated in the control segment included in the training apparatus in FIG. 1.

As the CPU 401 executes the aforementioned program, a functional block as shown in FIG. 7 is created within the control segment 400.

The control segment 400 includes a received information analyzing unit 411, a main control unit 412, a pulse wave analyzing unit 413, and a control data generating unit 414.

The received information analyzing unit 411 is for receiving, through the interface 404, the pulse wave data, the data from the input device, and the data about the pressure within the inflatable bag 120 from the pressure sensor 212 and analyzing them. When the data received by the received information analyzing unit 411 is either the pulse wave data or the data about the pressure within the inflatable bag 120, the data itself is transferred to the pulse wave analyzing unit 413. When the data received by the received information analyzing unit 411 is the data from the input device, the data analyzed by the received information analyzing unit 411 is sent to the main control unit 412.

The main control unit 412 is for controlling the entire control segment 400.

The main control unit 412 first carries out control to choose and execute either one of the two modes provided for this training apparatus. In this training apparatus, two modes: an automatic mode and a manual mode can be used.

The automatic mode can further be divided into two operations: pre-processing and normal processing.

The automatic mode is carried out when an input from the input device is given indicating that the automatic mode should be chosen. It is noted that information for specifying a first coefficient is also provided by using the input device before or after the input indicating that the automatic mode should be chosen, if any, is given. The first coefficient is for specifying a numeral equal to or larger than 0.2 but smaller than 1. The information for specifying the first coefficient may be the one that directly specifies a numeral equal to or larger than 0.2 but smaller than 1, such as 0.55 and 0.70. Alternatively, it may be information for use in choosing an appropriate one of a set of predetermined numerals that are smaller than 1, by 0.05 increments from 0.20.

The automatic mode is a mode in which gas pressures within the inflatable bag 120 for the KAATSU training are automatically determined in the KAATSU training.

In response to an input from the input device indicating that the automatic mode is to be used, the data representing the fact and the data for specifying the first coefficient are both supplied to the received information analyzing unit 411 through the interface 404. Then, the received information analyzing unit 411 analyzes the data and sends them to the main control unit 412, which activates the automatic mode. In this case, the main control unit 412 generates data about instructions for performing the automatic mode, and sends it to the control data generating unit 414 and the pulse wave analyzing unit 413. The main control unit 412 is adapted to send the first coefficient, which has been specified by the information for specifying the first coefficient, to the pulse wave analyzing unit 413 when the automatic mode is chosen.

Details of the automatic mode will be described below.

Next, the manual mode is described. The manual mode is performed when an input to choose the manual mode is entered with the input device. The manual mode is a mode in which gas pressures within the inflatable bag 120 for the KAATSU training are manually determined in the KAATSU training.

To choose the manual mode, provided are data representing information about how high the pressure within the inflatable bag 120 of which tight fitting band 100 is set and how long the subject pressure is to be continued, along with or subsequent to data representing information indicating that the manual mode is to be chosen. These data are supplied from the input device through the interface 404 to the received information analyzing unit 411. The received information analyzing unit 411 analyzes the data and sends them to the main control unit 412, which activates the manual mode. In this case, the main control unit 412 generates data about instructions to perform the manual mode, and sends it to the control data generating unit 414 along with the data representing the information about how high the pressure within the inflatable bag 120 of which tight fitting band 100 is set and how long the subject pressure is to be continued.

It is noted that the data representing information about how high the pressure within the inflatable bag 120 of which tight fitting band 100 is set and how long the subject pressure is to be continued, may be different from each other among the tight fitting bands 100. In addition, the data representing information about how high the pressure within the inflatable bag 120 of which tight fitting band 100 is set and how long the subject pressure is to be continued, do not necessarily indicate that the pressure within the inflatable bag 120 is kept constant. It may indicate that the pressure within the inflatable bag 120 is to be varied over time.

In response to the data supplied from the main control unit 412 indicating the automatic mode is to be performed, the pulse wave analyzing unit 413 receives the pulse wave data and the data about the pressure within the inflatable bag 120 through the cable 700, the interface 404, and the received information analyzing unit 411, during the time when the preprocessing for the automatic mode is carried out. Then, according to the pulse wave data, the magnitude of the pulse wave component at the time at which the maximum pulse wave pressure is produced and a first reference pressure are determined. How the pulse wave analyzing unit 413 detects them will be described in detail below. The pulse wave analyzing unit 413 sends the data about the determined first reference pressure to the control data generating unit 414 through the main control unit 412.

The control data generating unit 414 is for generating the control data for use in controlling the main device 200 according to the data about the first reference pressure that is received from the main control unit 412. The control data generating unit 414 transmits the generated control data through the interface 404 to the main device 200. As will be described below, the control data is also sent to the main control unit 412 as the case may be.

How the control data generating unit 414 generates the control data will be described below. In response to this, the pump control mechanism 220 of the main device 200 controls the individual pumps 210 according to that control data.

Next, how to use this training apparatus is described.

Upon performing the KAATSU training by using this training apparatus, the four tight fitting bands 100 are wrapped around compression target ranges on the limbs of the user. The two tight fitting bands 110A for arms are placed on the arms and the two tight fitting bands 100B for legs are placed on the legs. More specifically, the inflatable bag 120 is encircled once around the compression target range, and the excessive length of the belt 110 is further encircled two times around it. Thereafter, the fastening member 130 is used to fasten the end of the belt 110. Then, the tight fitting band 100A or 100B applies a given compression force to the arms or the legs, respectively. The compression force does not reach a pressure that is appropriate for the user to receive the KAATSU training.

Next, the four measuring segments 300 are placed at positions suitable for obtaining the pulse waves from the arms and the legs (more precisely, the pulse waves at a position near the compression target range or other area that is closer to the distal end of the limb) on which the four tight fitting bands 100 are placed. In this embodiment, the measuring segment 300 is rest at a position closer to the distal end of the limb than the tight fitting band 100 in such a manner that it contacts with the tight fitting band 100.

Next, the four tight fitting bands 100 are connected to the main device 200 via the connecting pipes 500, respectively. In addition, the four measuring segments 300 are connected to the control segment 400 via the cables 700, respectively. Furthermore, the control segment 400 and the main device 200 are connected to each other via the cable 600.

With this state, the KAATSU training is started.

Just before starting the KAATSU training, a user or a person who instruct a user the KAATSU training manipulates the input device to choose either the automatic mode or the manual mode and enters the information for specifying the first coefficient.

In the following description, for the purpose of simplification, described is the case where either one of the limbs is subjected to the KAATSU training. In practice, however, two or more limbs are subjected to the KAATSU training as described below. It is more common to do so when the tight fitting band 100 is rest on all the limbs of the user as in this embodiment. When two or more limbs are subjected to the KAATSU training, each limb may be subjected to the KAATSU training one after another without any overlapping in time or two or more limbs may be subjected to the KAATSU training at the same time. Alternatively, two or more limbs may be subjected to the KAATSU training, slightly delaying the timing with some overlap between the two time periods.

When the automatic mode is chosen, the data indicating that is sent to the main control unit 412 through the interface 404 and the received information analyzing unit 411. The main control unit 412 sends the data indicating that the automatic mode is to be activated, to the pulse wave analyzing unit 413 and the control data generating unit 414. In response to this data, the pulse wave analyzing unit 413 and the control data generating unit 414 begins the preprocessing of the automatic mode. In addition, the main control unit 412 sends the first coefficient to the pulse wave analyzing unit 413.

The first coefficient is a numeral equal to or larger than 0.2 but smaller than 1 as described above. However, this may be limited to a certain range. For example, the first coefficient may be limited to a numerical range between 0.2 and 0.9, both inclusive. When there is such a limitation, the main control unit 412 may reject the first coefficient represented by the information for specifying the first coefficient provided by using the input device if it is smaller than 0.2 or larger than 0.9, and then perform processing to prompt the user to re-enter it. The range of the first coefficient is not limited to the above. For example, the first coefficient may be determined within a numerical range between 0.4 and 0.6.

When the range of the first coefficient is limited, this limitation of the range of the first coefficient may be made only when a specific condition is satisfied. For example, the user may be requested to enter his or her characteristic properties (e.g., the age, sex, and athletic history of the user) by using the input device when the user enters the input to choose the automatic mode by using the input device, and the first coefficient may be limited only when the characteristic properties satisfy a specific condition.

In this embodiment, it is assumed that the first coefficient is tentatively set to 0.50.

For the preprocessing, the control data generating unit 414 generates the control data. The control data generating unit 414 sends the generated control data to the pump control mechanism 220 of the main device 200 and the main control unit 412 through the interface 404 and the cable 600. The control data sent to the pump control mechanism 220 in this embodiment indicates, but not limited thereto, that the pump 210 is directed to quickly (e.g., within 1 second) supply the air to the inflatable bag 120 until the air pressure within the inflatable bag 120 significantly exceeds an expected first reference pressure (e.g., approximately 1.5 to 2.0 times higher than a pressure that is expected to be the first reference pressure), then the pump 210 is directed to reduce the air pressure within the inflatable bag 120 over, for example, 5 to 10 seconds until the pressure becomes significantly smaller than the maximum pulse wave pressure (e.g., approximately 0.5 to 0.7 times lower than a pressure that is expected to the maximum pulse wave pressure).

In response to this data, the pump control mechanism 220 drives the pump 210 according to this data. Consequently, the pump 210 supplies the air to the inflatable bag 120 of the tight fitting band 100 that is associated to the pump 210, and then opens the valve to remove the air within the inflatable bag 120. As a result, the air pressure within the inflatable bag 120 of the tight fitting band 100 and the pressure applied to the compression target range by the tight fitting band 100 are once increased to a significantly higher level and then the air pressure within the inflatable bag 120 of the tight fitting band 100 and the pressure applied to the compression target range by the tight fitting band 100 are both reduced. The pressure within the inflatable bag 120 may be reduced continuously or stepwise (the pressure is kept at a constant level intermittently).

On the other hand, during the preprocessing, the pressure applied by the tight fitting band 100 to the compression target range to compress the compression target range fluctuates, so that the pulse wave also fluctuates accordingly. The measuring segment 300 continuously measures over time a predetermined parameter (in this embodiment, the parameter is the pressure that fluctuates along the fluctuation of the pulse waves, in which it is obtained by the measuring segment 300 through the skin) that fluctuates along the fluctuation of the magnitude of the ever-changing pulse wave, generates the pulse wave data representing the parameter, and sends it to the received information analyzing unit 411 through the cable 700 and the interface 404. The pulse wave analyzing unit 413 which has received it without any interruption determines the maximum pulse wave pressure and the first reference pressure.

How the pulse wave analyzing unit 413 determines the maximum pulse wave pressure and the first reference pressure is now described.

Figure 8:
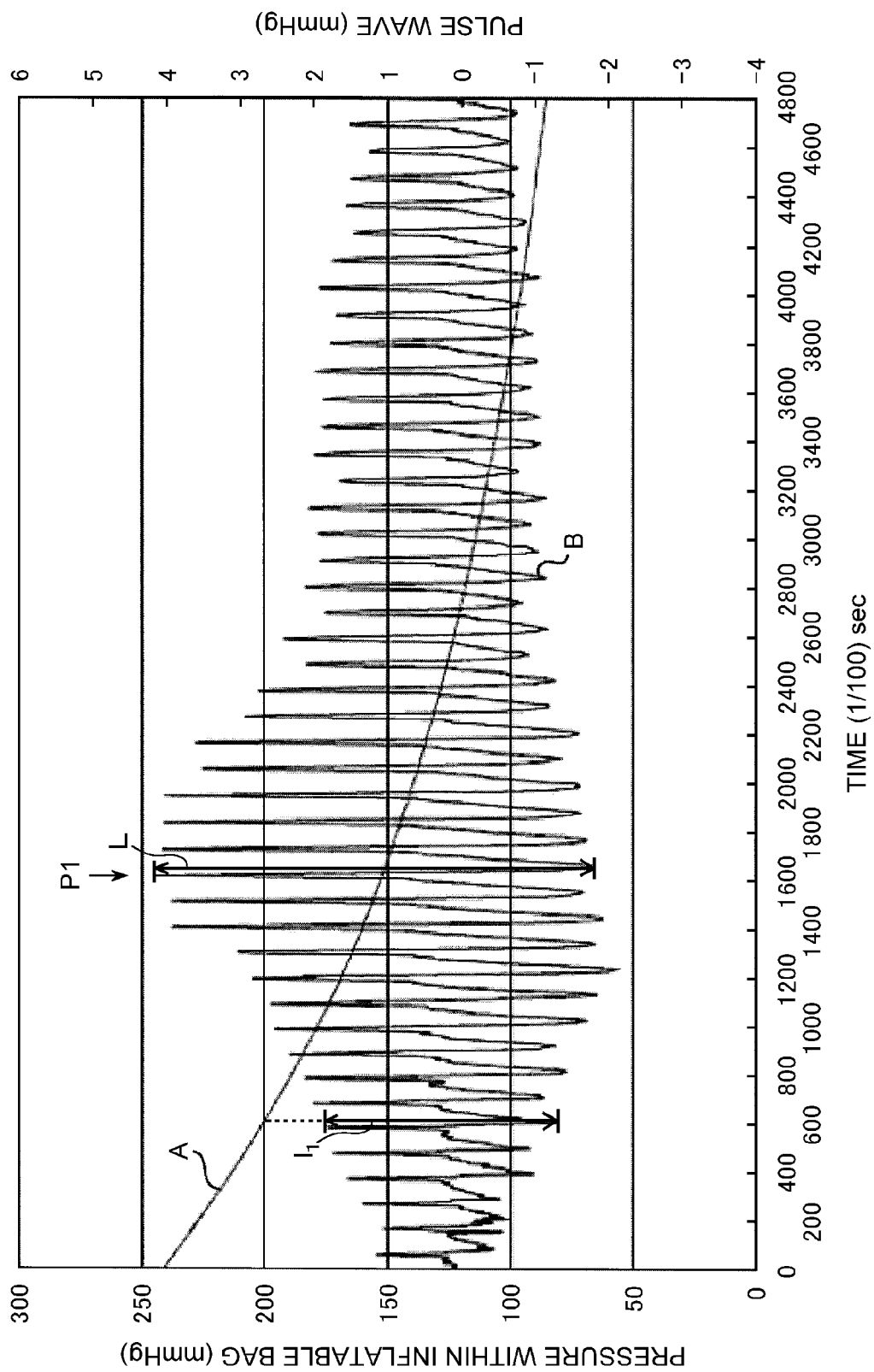
FIG. 8 is a view illustrating the fluctuation in magnitude of a pulse wave associated with the change in air pressure within the inflatable bag during preprocessing carried out by the training apparatus shown in FIG. 1.

FIG. 8 shows an example of a measured pulse wave. The shallow curve, downward sloping to the right, depicted by the symbol A in the figure represents the gas pressure (in mmHg) within the inflatable bag 120. On the other hand, the waveform with peak-to-peak amplitudes depicted by the symbol B in the figure represents the magnitude of the pulse wave component (in mmHg). The magnitude of the pulse wave component at a given time point is determined according to the peak-to-peak amplitude of the adjacent components.

The magnitude of the pulse wave components gradually increases as the pressure applied to the compression target range by the tight fitting band 100 to compress the compression target range is reduced, and turns to decrease after the pressure applied to the compression target range by the tight fitting band 100 to compress the compression target range (the pressure within the inflatable bag 120) becomes lower than a certain pressure. In FIG. 8, the increasing amplitude of the pulse wave begins to fall once it reaches the time point depicted by the symbol P1 in the figure. The pulse wave analyzing unit 413 continuously monitors the magnitude of the pulse wave components by using the pulse wave data as described above. The time point at which the increasing magnitude of the pulse wave components begins to fall is determined as the time point at which the magnitude of the pulse wave component reaches the maximum. It is noted that the pulse wave analyzing unit 413 may use the data representing the magnitude (s) of the pulse wave obtained before or around the time point depicted by the symbol P1 in the figure and differentiate, for example, the function about the magnitude of the pulse wave components with respect to time to calculate the time point at which the magnitude of the pulse wave component reaches the extreme value, which is determined (estimated) as the time point at which the pulse wave reaches the maximum. The pulse wave analyzing unit 413 determines the magnitude of the pulse wave component (L in FIG. 8) at the time point at which the pulse wave reaches the maximum (when the maximum pulse wave pressure is generated).

On the other hand, the first reference pressure is determined as follows. The pulse wave analyzing unit 413 stores thereon the data shown in FIG. 8, i.e., the data about the pressure within the inflatable bag 120 at a certain time period during the preprocessing and the data about the magnitude of the pulse wave components. Then, it detects the time point, after the determination of the magnitude of the pulse wave component L when the maximum pulse wave pressure is generated, at which the pulse wave component has the magnitude equal to the magnitude of the pulse wave component L at that point multiplied by the first coefficient (in this embodiment, 0.50) and the pressure within the inflatable bag 120 is higher than the maximum pulse wave pressure. In this embodiment, it is the time point at which the pulse wave reaches $l_1$. The pressure within the inflatable bag 120 at that time is considered as the first reference pressure. In FIG. 8, the pressure within the inflatable bag 120, i.e., approximately 200 mmHg, at the time point at which the extended line from $l_1$ crosses the curve representing the pressure within the inflatable bag 120, is determined as the first reference pressure.

The pulse wave analyzing unit 413 generates the data representing the first reference pressure and sends it to the main control unit 412.

This completes the preprocessing.

Next, the main control unit 412 sends the data to the control data generating unit 414 indicating that the normal processing should be performed. In this event, the main control unit 412 sends the data representing the first reference pressure to the control data generating unit 414, wherein the first reference pressure is used as a reference associated with the air within the inflatable bag 120 during the normal processing.

In response to the instruction to perform the normal processing, the control data generating unit 414 generates the control data and sends it to the pump control mechanism 220 of the main device 200 through the interface 404 and the cable 600. The control data is for setting the air pressure within the inflatable bag 120 into a predetermined range above or below the first reference pressure. For example, the control data may be for keeping the pressure within the inflatable bag 120 at the level of the first reference pressure, or alternatively, for keeping the pressure within the inflatable bag 120 in a range of 10 percents above or below the first reference pressure, or alternatively, for changing the pressure within the inflatable bag 120 in a range of 10 percents above or below the first reference pressure in every 30 seconds. The control data also includes the data about the time duration during which the KAATSU training is to be performed. The time duration is often about 10 to 15 minutes for the KAATSU training of the arms while it is often about 15 to 20 minutes for the KAATSU training of the legs.

In response to this control data, the pump control mechanism 220 drives the pump(s) 210 according to the instruction indicated by the control data. This allows the tight fitting band 100 to keep the air pressure within the inflatable bag 120 at an appropriate level. Thus, according to this training apparatus, the KAATSU training can be performed safely and effectively. The pump control mechanism 220 drives the pump(s) 210 according to the instruction indicated by the control data while monitoring the pressure within the inflatable bag 120 at that time point by using the pressure sensor 212.

After the lapse of a predetermined time period, the pump 210 opens the valve to remove the air from the inflatable bag 120. It is noted that the training apparatus may have a lamp or a buzzer as a means to notify the user of the completion of the KAATSU training. The lighting or sound of the lamp or the buzzer, respectively, may be used to notify him or her of the completion of the KAATSU training.

When the manual mode is chosen, the data indicating that and the data representing information about how high the pressure within the inflatable bag 120 of the tight fitting band 100 is set and how long the subject pressure is to be continued, are supplied by, for example, a person who instructs the user the KAATSU training, with the input device. These data are received by the received information analyzing unit 411 which analyzes the data. The received information analyzing unit 411 sends the analyzed result to the main control unit 412.

In response to this data, the main control unit 412 sends that data along with the data instructing the activation of the manual mode, to the control data generating unit 414. In response to the data about this instruction, the control data generating unit 414 generates the control data which indicates that instruction as well as the instruction to drive the pump 210 in order to keep the pressure within the inflatable bag 120 by the tight fitting band 100 at the given level for the given period of time, according to the data received from the main control unit 412. The generated control data is sent to the pump control mechanism 220 through the interface 404 and the cable 600.

In response to this control data, the pump control mechanism 220 drives the pump 210 according to the instruction indicated by the control data. This causes the air pressure within the inflatable bag 120 of the tight fitting band 100 to change following the conditions given by, for example, the user. In this case, the air pressure within the inflatable bag 120 may exceeds the aforementioned maximum pulse wave pressure. However, the safeness and effectiveness of the KAATSU training can be maintained as long as a person who has special knowledge about the KAATSU training, such as a physician, manipulates the input device.

After the lapse of a predetermined time period, the pump 210 opens the valve to remove the air from the inflatable bag 120. The lighting or sound of the lamp or the buzzer, respectively, can be used to notify the user of the completion of the KAATSU training, as described above.

During the KAATSU training in either the automatic mode or the manual mode, the user may keep rest or may do light exercises.

The preprocessing in the automatic mode may be used only when the user performs the KAATSU training by using this training apparatus for the first time, and may be omitted during the second and later KAATSU training by means of using the maximum pulse wave pressure that is determined during the first KAATSU training. However, the maximum pulse wave pressure may be varied depending on, for example, the general health of the user, so that it is preferable that the pulse wave be determined at the time when the maximum pulse wave pressure is produced every time when the KAATSU training is performed by using this training apparatus.

Modified Version

Although the training apparatus according to the first embodiment is as described above, the preprocessing carried out by the training apparatus in the first embodiment may be modified as follows. Briefly, in the preprocessing that is carried out when the automatic mode is chosen, the training apparatus according to the first embodiment raises the gas pressure within the inflatable bag 120 to a pressure that is expected to be significantly higher than the first reference pressure, and thereafter reduces it. On the other hand, in this modified version, the pressure is controlled to be gradually increased from a pressure (e.g., an ordinary pressure) that is obviously lower than the maximum pulse wave pressure. It is noted that the training apparatus in this modified version is identical in hardware configuration to the training apparatus according to the first embodiment.

Now, the automatic mode to be used in the modified version is described.

In the modified version, when the automatic mode is chosen, the data indicating that is sent to the main control unit 412 through the interface 404 and the received information analyzing unit 411. The main control unit 412 sends the data indicating that the automatic mode is to be activated, to the pulse wave analyzing unit 413 and the control data generating unit 414. In response to this data, the pulse wave analyzing unit 413 and the control data generating unit 414 begins the preprocessing of the automatic mode.

For the preprocessing, the control data generating unit 414 generates the control data. In the modified version, this control data is different from the one in the first embodiment.

In the modified version, the control data indicates that the pump 210 is directed to increase the air pressure within the inflatable bag 120 from the ordinary pressure to a pressure that is significantly higher than the first reference pressure (e.g., approximately 1.5 to 2.0 times higher than a pressure that is expected to be a first pulse wave pressure) over an appropriate period of time (e.g., 5 to 10 seconds), and then to reduce the air pressure within the inflatable bag 120 to the ordinary pressure. The control data generating unit 414 sends the generated control data to the pump control mechanism 220 of the main device 200 and the main control unit 412 through the interface 404 and the cable 600.

In response to this data, the pump control mechanism 220 drives the pump 210 according to this data. Consequently, the pump 210 supplies the air to the inflatable bag 120 of the tight fitting band 100 that is associated to the pump 210, increases the air pressure within the inflatable bag 120 to a pressure that is significantly higher than the first reference pressure, and then removes the air from the inflatable bag 120.

During the time duration when the pressure within the inflatable bag 120 is at an increased level, the pressure applied by the tight fitting band 100 to the compression target range to compress the compression target range fluctuates, so that the pulse wave also fluctuates accordingly. The measuring segment 300 continuously measures over time a predetermined parameter that fluctuates along the fluctuation of the magnitude of the ever-changing pulse wave, generates the pulse wave data representing the parameter, and sends it to the received information analyzing unit 411 through the cable 700 and the interface 404. The pulse wave analyzing unit 413 which has received it without any interruption determines the time point at which the pulse wave reaches the maximum, according to the pulse wave data. In this event, the data about the pressure within the inflatable bag 120 is also sent from the pressure sensor 212 to the pulse wave analyzing unit 413.

Figure 9:
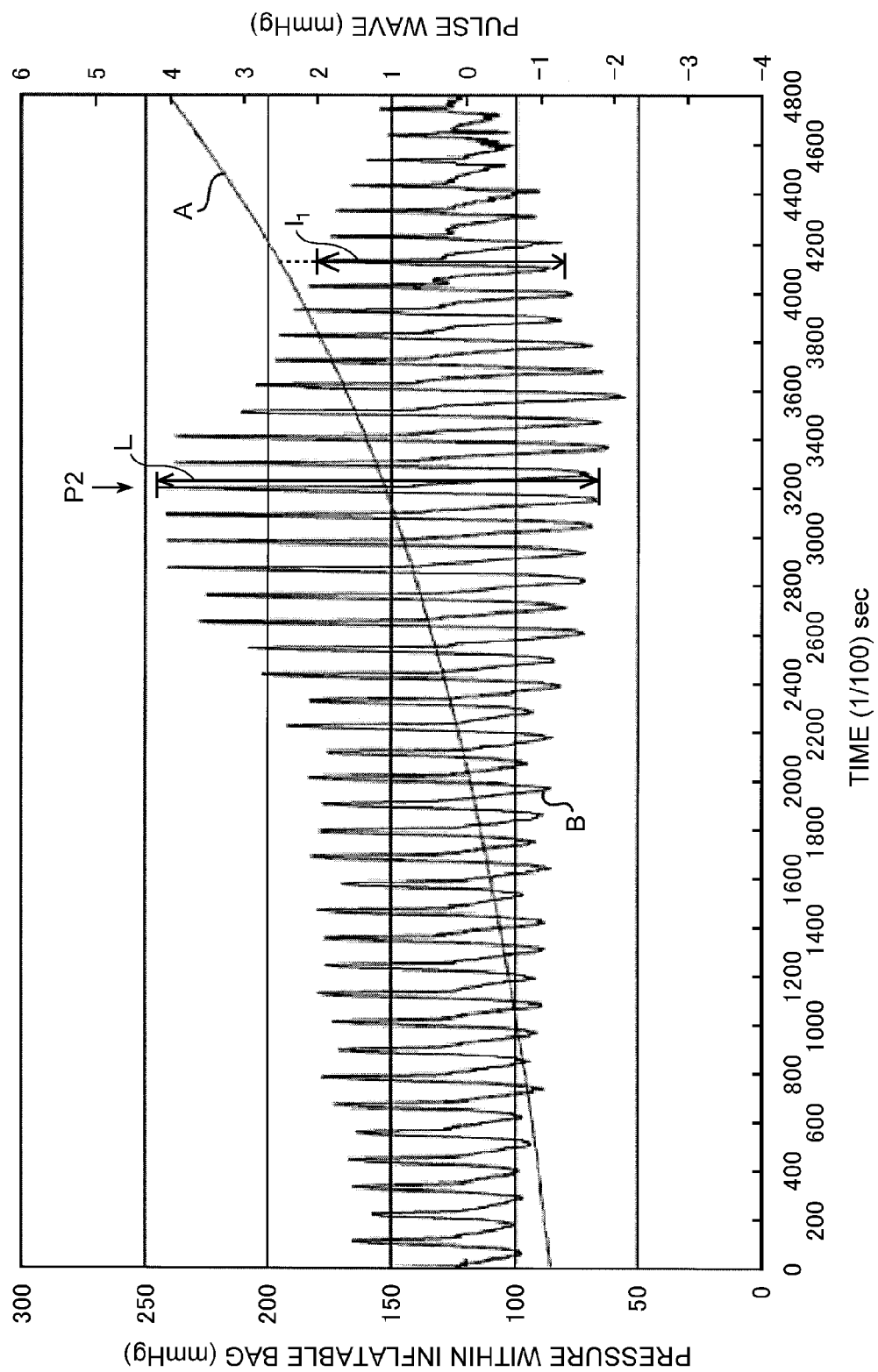
FIG. 9 is a view illustrating the fluctuation in magnitude of a pulse wave associated with the change in air pressure within the inflatable bag during preprocessing carried out by the training apparatus shown in FIG. 1.

In this modified version, the pulse wave analyzing unit 413 determines the time point at which the pulse wave reaches the maximum, in the following manner. FIG. 9 shows an example of the measured pulse wave. In the figure, the symbol A represents the gas pressure within the inflatable bag 120 (in mmHg) while the symbol B represents the magnitude of the pulse wave component (in mmHg).

As in this modified version, when the pressure to compress the limb is increased by means of increasing the gas pressure within the inflatable bag 120, the amplitude of the pulse wave components is increased gradually as shown in FIG. 9. When this pressure exceeds a certain level, then it begins to fall. In FIG. 9, the increasing amplitude of the pulse wave begins to fall once it reaches the time point depicted by the symbol P2 in the figure. The pulse wave analyzing unit 413 in the modified version continuously monitors the magnitude of the pulse wave components by using the pulse wave data as described above. The time point when the increasing magnitude of the pulse wave components begins to fall is determined as the time point when the magnitude of the pulse wave component reaches the maximum. It is noted that the pulse wave analyzing unit 413 may use the data representing the magnitude (s) of the pulse wave obtained before or around the time point depicted by the symbol P2 in the figure and differentiate, for example, the function about the magnitude of the pulse wave component with respect to time to calculate the time point at which the magnitude of the pulse wave component reaches the extreme value, which is determined (estimated) as the time point when the pulse wave reaches the maximum.

At any rate, the pulse wave analyzing unit 413 measures the pulse wave at the time point when the magnitude of the pulse wave component reaches the maximum (when the maximum pulse wave pressure is generated).

On the other hand, the first reference pressure is determined as follows. The pulse wave analyzing unit 413 stores thereon the data shown in FIG. 9, i.e., the data about the pressure within the inflatable bag 120 at a certain time period during the preprocessing and the data about the magnitude of the pulse wave component (at least those occurred after the time point when the maximum pulse wave pressure is generated). Then, it detects the time point, after the determination of the magnitude of the pulse wave component L when the maximum pulse wave pressure is generated, when the pulse wave component has the magnitude equal to the magnitude of the pulse wave component L at that point multiplied by the first coefficient (in this embodiment, 0.50) and the pressure within the inflatable bag 120 is higher than the maximum pulse wave pressure. In this embodiment, it is the time point when the pulse wave reaches $l_1$ in FIG. 9. The pressure within the inflatable bag 120 at that time is considered as the first reference pressure. In FIG. 9, the pressure within the inflatable bag 120, i.e., approximately 190 mmHg, at the time point where the extended line from $l_1$ crosses the curve representing the pressure within the inflatable bag 120, is determined as the first reference pressure.

In the modified version, the pressure within the inflatable bag 120 is once increased to a predetermined pressure that is significantly higher than the maximum pulse wave pressure, and then the air pressure within the inflatable bag 120 is reduced to the ordinary pressure. However, the pump control mechanism 220 may carry out the control to remove the air from the inflatable bag 120 at the time point at which the pulse wave analyzing unit 413 determines the first reference pressure. In this case, the control data generating unit 414 generates such control data that directs the pump control mechanism 220 to carry out the control for such a purpose.

Second Embodiment

The training apparatus according to the second embodiment is basically identical to the one in the first embodiment. In particular, the training apparatus according to the second embodiment is identical to the one in the first embodiment in terms of the hardware configuration described with reference to FIGS. 1 to 6 in the first embodiment.

In addition, the training apparatus according to the second embodiment is also identical to the one in the first embodiment in terms of the functional block shown in FIG. 7. However, the functions of the main control unit 412 and the pulse wave analyzing unit 413 that are provided when the automatic mode is chosen in the second embodiment are slightly different from those provided when the automatic mode is chosen in the first embodiment. In addition, the second embodiment is different from the first embodiment in terms of the information entered by using the input device when the automatic mode is chosen, as well as the information which the interface 404 and the received information analyzing unit 411 receives from the input device.

In the first embodiment, when the data for use in choosing the automatic mode is entered by using the input device, the information for specifying the first reference pressure is also entered by using the input device.

Instead, in the second embodiment, information for specifying the first and second coefficients is entered by using the input device in addition to the data for use in choosing the automatic mode.

The first and second coefficients are both for specifying a numeral that is equal to or larger than 0.2 but smaller than 1, provided that the second coefficient is larger than the first coefficient.

The information for specifying the first and second coefficients may be the information for separately specifying the first and second coefficients. Each of these information may be the one that directly specifies a numeral equal to or larger than 0.2 but smaller than 1, such as 0.55 and 0.70. Alternatively, it may be information for use in choosing an appropriate one of a set of predetermined numerals that are smaller than 1, by 0.05 increments from 0.20. The information for specifying the first and second coefficients may be a single piece of information about an in-between numeral (a numeral not smaller than the first coefficient and not larger than the second coefficient) as described below.

The data for choosing the automatic mode and the information for specifying the first and second coefficients are sent to the received information analyzing unit 411 through the interface 404.

The received information analyzing unit 411 analyzes these data and sends them to the main control unit 412. This activates the automatic mode. In this case, the main control unit 412 generates the data about an instruction to activate the automatic mode, and sends it to the control data generating unit 414 and the pulse wave analyzing unit 413. In addition, the main control unit 412 sends the first and second coefficients that are determined by using the information for specifying the first and second coefficients, to the pulse wave analyzing unit 413, when the automatic mode is chosen.

The main control unit 412 specifies the first and second coefficients in the following manner.

When the information for specifying the first and second coefficients is the information for separately specifying the first and second coefficients, then the main control unit 412 determines the first and second coefficients as in the case of the first embodiment.

When the information for specifying the first and second coefficients is the information about the aforementioned in-between numeral, the main control unit 412 determines both the first and second coefficients by means of, for example, performing an arithmetic operation with an in-between numeral according to the numeral specified by that single piece of information. With this arithmetic operation, for example, the in-between numeral itself that is specified by the information for specifying the in-between numeral may be used as the first coefficient, and a numeral obtained by means of adding a predetermined numeral that is smaller than 1 thereto or multiplying it with a predetermined numeral larger than 1 (e.g., an appropriate numeral between 1.15 and 1.30) may be used as the second coefficient. Alternatively, with this arithmetic operation, a subtraction result obtained by subtracting a predetermined numeral that is smaller than 1 (e.g., an appropriate numeral between 0.05 and 0.20) from the in-between numeral that is specified by the information for specifying the in-between numeral may be used as the first coefficient, and a sum of a predetermined numeral that is smaller than 1 (which may or may not be the same as the subtracted one) and the in-between numeral may be used as the second coefficient. Alternatively, with the arithmetic operation, a product obtained by multiplying the in-between numeral with a predetermined numeral that is smaller than 1 (e.g., an appropriate numeral between 0.85 and 0.95) may be used as the first coefficient, and a product obtained by multiplying the in-between numeral with a predetermined numeral that is larger than 1 (e.g., an appropriate numeral between 1.05 and 1.15) may be used as the second coefficient.

In the second embodiment, the first and second coefficients may be limited to a certain range. The first coefficient may be limited to a numerical range between 0.4 and 0.6. The second coefficient may be defined as a numeral not larger than 0.9. Alternatively, it may be defined as a numeral between 0.5 and 0.7. A combination of the first coefficient of between 0.4 and 0.6 and the second coefficient of between 0.5 and 0.7 has broad utilities.

When the information for specifying the first and second coefficients is the information for separately specifying the first and second coefficients, and when either one of the first and second coefficients represented by the information does not fall within the aforementioned limited range, the main control unit 412 may reject the input thereof as in the case of the first embodiment. In addition, when the first coefficient is larger than the second coefficient, the main control unit 412 may reject the input thereof.

When the information for specifying the first and second coefficients is the information for specifying the in-between numeral, and when either one of the first and second coefficients obtained from the in-between numeral specified by the information by using an arithmetic operation as described above does not fall within the aforementioned limited range, the main control unit 412 may reject the input of the aforementioned information for specifying the in-between numeral.

The operations of the control data generating unit 414, the pump control mechanism 220, and the pump 210 during the preprocessing in the second embodiment are similar to those in the first embodiment.

In the first embodiment, the pulse wave analyzing unit 413 specifies the maximum pulse wave pressure and the first reference pressure during the preprocessing. On the other hand, in the second embodiment, a second reference pressure is also determined.

How the pulse wave analyzing unit 413 determines the maximum pulse wave pressure as well as the first and second reference pressures is now described. The way to determine the first reference pressure is identical to the one as described in the first embodiment, and the second reference pressure is also determined in a similar manner.

Figure 10:
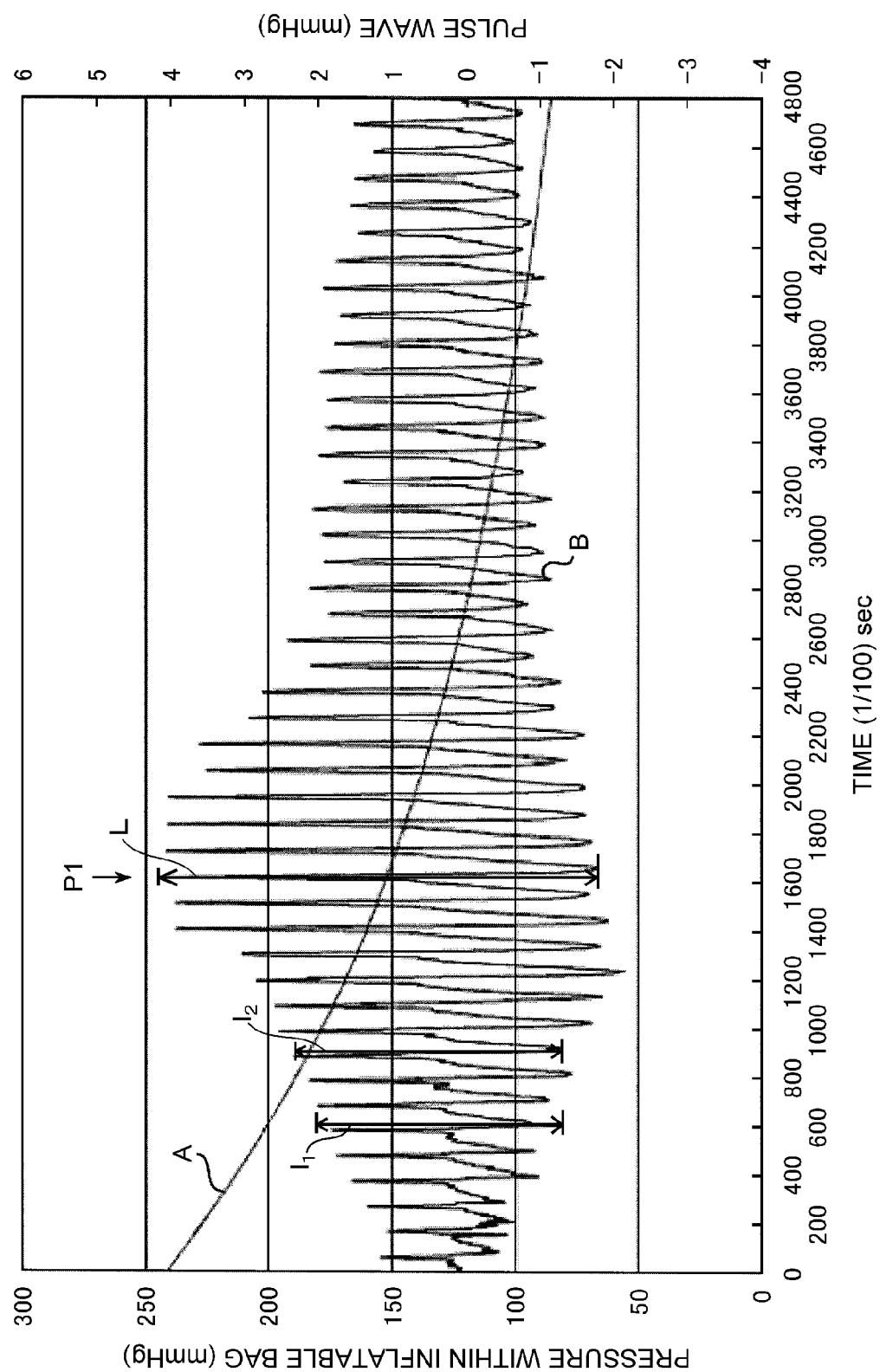
FIG. 10 is a view illustrating the fluctuation in magnitude of a pulse wave associated with the change in air pressure within the inflatable bag during preprocessing carried out by the training apparatus according to the second embodiment.

FIG. 10 shows an example of a measured pulse wave. The curve depicted by the symbol A in the figure represents the gas pressure (in mmHg) within the inflatable bag 120. On the other hand, the curve depicted by the symbol B in the figure represents the magnitude of the pulse wave components (in mmHg).

This example is a case in which the pressure within the inflatable bag 120 is once increased to a level higher than a pressure that is expected to be the first reference pressure, and then the pressure within the inflatable bag 120 is reduced.

The magnitude of the pulse wave components gradually increases as the pressure applied to the compression target range by the tight fitting band 100 is reduced, and turns to decrease after the pressure applied to the compression target range by the tight fitting band 100 to compress the compression target range (the pressure within the inflatable bag 120) becomes lower than a certain pressure. In FIG. 10, the increasing amplitude of the pulse wave begins to fall once it reaches the time point depicted by the symbol P1 in the figure. The pulse wave analyzing unit 413 continuously monitors the magnitude of the pulse wave components by using the pulse wave data as described above. The time point at which the increasing magnitude of the pulse wave components begins to fall is determined as the time point at which the magnitude of the pulse wave component reaches the maximum. The pulse wave analyzing unit 413 determines the magnitude of the pulse wave component (L in FIG. 10) at the time point at which the pulse wave reaches the maximum (when the maximum pulse wave pressure is generated).

On the other hand, the first reference pressure is determined as follows. The pulse wave analyzing unit 413 stores thereon the data shown in FIG. 10, i.e., the data about the pressure within the inflatable bag 120 at a certain time period during the preprocessing and the data about the magnitude of the pulse wave component. Then, it detects the time point, after the determination of the magnitude of the pulse wave component L when the maximum pulse wave pressure is generated, at which the pulse wave component has the magnitude equal to the magnitude of the pulse wave component L at that point multiplied by the first coefficient (in this embodiment, tentatively 0.55) and the pressure within the inflatable bag 120 is higher than the maximum pulse wave pressure. In this embodiment, it is the time point at which the pulse wave reaches $l_1$. The pressure within the inflatable bag 120 at that time is considered as the first reference pressure. In FIG. 10, the pressure within the inflatable bag 120, i.e., approximately 200 mmHg, at the time point at which the extended line from $l_1$ crosses the curve representing the pressure within the inflatable bag 120, is determined as the first reference pressure.

Likewise, for the second reference pressure, it detects the time point, after the determination of the magnitude of the pulse wave component L when the maximum pulse wave pressure is generated, at which the pulse wave component has the magnitude equal to the magnitude of the pulse wave component L at that point multiplied by the second coefficient (in this embodiment, tentatively 0.62) and the pressure within the inflatable bag 120 is higher than the maximum pulse wave pressure. In this embodiment, it is the time point at which the pulse wave reaches $l_2$. The pressure within the inflatable bag 120 at that time is considered as the second reference pressure. In FIG. 10, the pressure within the inflatable bag 120, i.e., approximately 180 mmHg, at the time point at which the extended line from $l_2$ crosses the curve representing the pressure within the inflatable bag 120, is determined as the second reference pressure.

In the second embodiment, as in the case of the modified version of the first embodiment, the pressure within the inflatable bag 120 may be reduced to a pressure (e.g., an ordinary pressure) that is obviously lower than the maximum pulse wave pressure, and then the pressure within the inflatable bag 120 is increased, during which process the first and second reference pressures are determined. In such a case, the first and second reference pressures may be determined according to the modified version of the first embodiment.

The pulse wave analyzing unit 413 generates the data of the first and second reference pressures and sends them to the main control unit 412, which completes the preprocessing in the second embodiment.

In the first embodiment, when the normal processing is started, the main control unit 412 sends, to the control data generating unit 414, the data indicating that the normal processing should be performed and the data about the first reference pressure. In the second embodiment, the main control unit 412 sends the data about the second reference pressure along with these data to the control data generating unit 414.

In response to the instruction to perform the normal processing, the control data generating unit 414 generates the control data and sends it to the pump control mechanism 220 of the main device 200 through the interface 404 and the cable 600.

The control data uses the first reference pressure as the upper limit and the second reference pressure as the lower limit. The control data is for setting the air pressure within the inflatable bag 120 into a predetermined range above or below the first reference pressure to the second reference pressure. For example, the control data may be for keeping the pressure within the inflatable bag 120 at the level of the first reference pressure or the second reference pressure, or alternatively, for changing the pressure within the inflatable bag 120 between the first reference pressure and the second reference pressure in every 30 seconds, or alternatively, for changing the pressure within the inflatable bag 120 from the middle between the first reference pressure and the second reference pressure, with an amplitude being equal to half the difference between the first reference pressure and the second reference pressure in one-minute periods. The control data also includes the data about the time duration during which the KAATSU training is to be performed, as in the case of the first embodiment.

In response to this control data, the pump control mechanism 220 drives the pump(s) 210 according to the instruction indicated by the control data. This allows the tight fitting band 100 to keep the air pressure within the inflatable bag 120 at an appropriate level.

An operation to complete the KAATSU training is similar to the one described in the first embodiment.

The invention claimed is:

1. A training apparatus comprising:
a tight fitting band including a belt having a length that is enough to be wrapped around a predetermined region of muscles of a limb; fastening means for fastening said belt with said belt being wrapped around said predetermined region of muscles; and an inflatable bag provided in or on said belt, said inflatable bag being adapted to apply a predetermined compression pressure to said predetermined region of muscles by means of filling said inflatable bag with a gas to fully compress the veins and not fully compress the arteries of said predetermined region of muscles while said belt that has been wrapped around said predetermined region of muscles is fastened by said fastening means;
pressure setting means that is capable of setting a gas pressure within said inflatable bag at a predetermined pressure;
control means for controlling said pressure setting means in order to change said compression pressure; and
pulse wave measuring means for measuring a predetermined parameter at a position near said predetermined region of muscles or a position closer to the distal end of the limb than said predetermined region of muscles, to generate a pulse wave data about the parameter, the parameter fluctuating along with the fluctuation of the magnitude of an arterial pulse wave that is changed in response to said compression pressure,
said control means being adapted to direct said pressure setting means to perform preprocessing and normal processing,
said control means being also adapted to, upon said preprocessing, control said pressure setting means so that said pressure setting means changes the gas pressure within said inflatable bag;
determine a pulse wave component at a time point at which the maximum pulse wave pressure is produced after receiving a plurality of said pulse wave data from said pulse wave measuring means during the time period when the pressure within said inflatable bag is changing; and
determine a first reference pressure which is the pressure within the inflatable bag at a time point when such a pulse wave component is produced that has an amplitude obtained by means of multiplying the amplitude of the pulse wave component at the time point at which said maximum pulse wave pressure is produced with a predetermined first coefficient that is equal to or larger than 0.2 but smaller than 1, the first reference pressure being larger than the pressure within said inflatable bag at the time point at which said maximum pulse wave pressure is produced,
said control means being adapted to, upon said normal processing, control said pressure setting means so that said pressure setting means keeps the gas pressure within said inflatable bag in a predetermined range above or below said the first reference pressure,
wherein said tight fitting band includes a plurality of tight fitting bands,
said pulse wave measuring means being equal in number to said tight fitting bands, said pressure setting means being associated with respective one of said tight fitting bands, said pulse wave measuring means being adapted to measure said parameter that fluctuates along with the fluctuation of the magnitude of the pulse wave at a position near a predetermined region of muscles or a position closer to the distal end of the limb than the predetermined region of muscles around which the respective tight fitting bands are wrapped that are associated with the pulse wave measuring means, to generate a pulse wave data about the parameter,
said pressure setting means being equal in number to said tight fitting bands, said pressure setting means being associated with respective one of said tight fitting bands,
said control means being adapted to control, upon said preprocessing, said pressure setting means to determine the pulse wave component at the time point at which said maximum pulse wave pressure is produced and said first reference pressure for each of the limbs, said control means being adapted to control, upon said normal processing, each of said pressure setting means that are associated with said tight fitting bands, respectively, for compressing the respective limbs, in such a manner that the gas pressure within said inflatable bag of the tight fitting band associated with the pressure setting means falls within a predetermined range above or below said first reference pressure that is determined for the limb for which the associated tight fitting band is to be used.

2. The training apparatus as claimed in claim 1, wherein said control means is adapted to set said first coefficient at a numeral that is not larger than 0.9.

3. The training apparatus as claimed in claim 1, wherein said control means is adapted to set said first coefficient at a numeral between 0.4 and 0.6.

4. The training apparatus as claimed in claim 1, wherein said control means is adapted to, upon said normal processing, control said pressure setting means so that said pressure setting means maintains the gas pressure within said inflatable bag at said the first reference pressure.

5. A training apparatus comprising:
a tight fitting band including a belt having a length that is enough to be wrapped around a predetermined region of muscles of a limb; fastening means for fastening said belt with said belt being wrapped around said predetermined region of muscles; and an inflatable bag provided in or on said belt, said inflatable bag being adapted to apply a predetermined compression pressure to said predetermined region of muscles by means of filling said inflatable bag with a gas to fully compress the veins and not fully compress the arteries of said predetermined region of muscles while said belt that has been wrapped around said predetermined region of muscles is fastened by said fastening means;
pressure setting means that is capable of setting a gas pressure within said inflatable bag at a predetermined pressure;
control means for controlling said pressure setting means in order to change said compression pressure; and
pulse wave measuring means for measuring a predetermined parameter at a position near said predetermined region of muscles or a position closer to the distal end of the limb than said predetermined region of muscles, to generate a pulse wave data about the parameter, the parameter fluctuating along with the fluctuation of the magnitude of an arterial pulse wave that is changed in response to said compression pressure,
said control means being adapted to direct said pressure setting means to perform preprocessing and normal processing,
said control means being also adapted to, upon said preprocessing, control said pressure setting means so that said pressure setting means changes the gas pressure within said inflatable bag;
determine a pulse wave component at a time point at which the maximum pulse wave pressure is produced after receiving a plurality of said pulse wave data from said pulse wave measuring means during the time period when the pressure within said inflatable bag is changing; and
determine a first reference pressure which is the pressure within the inflatable bag at a time point when such a pulse wave component is produced that has an amplitude obtained by means of multiplying the amplitude of the pulse wave component at the time point at which said maximum pulse wave pressure is produced with a predetermined first coefficient that is equal to or larger than 0.2 but smaller than 1, and a second reference pressure which is the pressure within the inflatable bag at a time point when such a pulse wave component is produced that has an amplitude obtained by means of multiplying the amplitude of the pulse wave component at the time point at which said maximum pulse wave pressure is produced with a predetermined second coefficient that is equal to or larger than 0.2 and larger than said first coefficient, the first reference pressure being larger than the pressure within said inflatable bag at the time point at which said maximum pulse wave pressure is produced, the second reference pressure being larger than the pressure within said inflatable bag at the time point at which said maximum pulse wave pressure is produced,
said control means being adapted to, upon said normal processing, control said pressure setting means so that said pressure setting means keeps the gas pressure within said inflatable bag in a predetermined range from said the first reference pressure to said the second reference pressure,
wherein said tight fitting band includes a plurality of tight fitting bands,
said pulse wave measuring means being equal in number to said tight fitting bands, said pressure setting means being associated with respective one of said tight fitting bands, said pulse wave measuring means being adapted to measure said parameter that fluctuates along with the fluctuation of the magnitude of the pulse wave at a position near a predetermined region of muscles or a position closer to the distal end of the limb than the predetermined region of muscles around which the respective tight fitting bands are wrapped that are associated with the pulse wave measuring means, to generate a pulse wave data about the parameter,
said pressure setting means being equal in number to said tight fitting bands, said pressure setting means being associated with respective one of said tight fitting bands,
said control means being adapted to control, upon said preprocessing, said pressure setting means to determine the pulse wave component at the time point at which said maximum pulse wave pressure is produced, said first reference pressure, and said second reference pressure, for each of the limbs, said control means being adapted to control, upon said normal processing, each of said pressure setting means that are associated with said tight fitting bands, respectively, for compressing the respective limbs, in such a manner that the gas pressure within said inflatable bag of the tight fitting band associated with the pressure setting means falls within a predetermined range between said first reference pressure and said second reference pressure that are determined for the limb for which the associated tight fitting band is to be used.

6. The training apparatus as claimed in claim 5, wherein said control means is adapted to set said first coefficient at a numeral between 0.4 and 0.6.

7. The training apparatus as claimed in claim 1, further comprising means for entering information for specifying said first coefficient;
said control means being adapted to determine said first coefficient by means of the information entered through said means for entering the information for specifying said first coefficient.

8. The training apparatus as claimed in claim 5, wherein said control means is adapted to set said second coefficient at a numeral that is not larger than 0.9.

9. The training apparatus as claimed in claim 5, wherein said control means is adapted to set said second coefficient at a numeral between 0.5 and 0.7.

10. The training apparatus as claimed in claim 5, further comprising means for entering information for specifying said second coefficient;
said control means being adapted to determine said second coefficient by means of the information entered through said means for entering the information for specifying said second coefficient.

11. The training apparatus as claimed in claim 5, further comprising means for entering information for specifying an in-between numeral which is a numeral not smaller than said first coefficient and not larger than said second coefficient, said control means being adapted to determine both said first coefficient and said second coefficient according to one information entered through said means for entering the information for specifying said in-between numeral.

12. The training apparatus as claimed in claim 11, wherein said control means uses results obtained by subtracting and adding a predetermined numeral that is smaller than 1 from and to the numeral that is specified by one information entered through said means for entering the information for specifying said in-between numeral, as the first coefficient and the second coefficient, respectively.

13. The training apparatus as claimed in claim 11, wherein said control means uses results obtained by multiplying the numeral that is specified by one information entered through said means for entering the information for specifying said in-between numeral with a predetermined numeral that is smaller than 1 and a predetermined numeral that is larger than 1, as the first coefficient and the second coefficient, respectively.

14. The training apparatus as claimed in claim 1, wherein said control means is adapted to, upon said preprocessing, control said pressure setting means in such a manner that said pressure setting means increases the pressure within said inflatable bag to a level that is higher than a pressure expected to exceed the first reference pressure, and then reduces the pressure within said inflatable bag.

15. The training apparatus as claimed in claim 14, wherein said control means is adapted to continuously receive said pulse wave data from said pulse wave measuring means during the time period when the pressure within said inflatable bag is decreasing in said preprocessing, and determine a pulse wave component at the time point at which the maximum pulse wave pressure is produced when the pulse wave component reaches the maximum, from the previous pulse wave data, when said pulse wave data indicates that said magnitude of the pulse wave component becomes smaller than the previous one.

16. The training apparatus as claimed in claim 14, wherein said control means is adapted to continuously receive said pulse wave data from said pulse wave measuring means during the time period when the pressure within said inflatable bag is decreasing in said preprocessing, and determine, as the maximum pulse wave pressure, an immediately preceding gas pressure within said inflatable bag when said pulse wave data indicates that said magnitude of the pulse wave component becomes smaller than the previous one.

17. The training apparatus as claimed in claim 1, wherein said control means is adapted to, upon said preprocessing, control said pressure setting means in such a manner that said pressure setting means reduces the pressure within said inflatable bag to a level that is lower than a pressure expected to be lower than the maximum pulse wave pressure, and then increases the pressure within said inflatable bag.

18. The training apparatus as claimed in claim 17, wherein said control means is adapted to continuously receive said pulse wave data from said pulse wave measuring means during the time period when the pressure within said inflatable bag is increasing in said preprocessing, and determine a pulse wave component at the time point at which the maximum pulse wave pressure is produced when the pulse wave component reaches the maximum, from the previous pulse wave data, when said pulse wave data indicates that said magnitude of the pulse wave component becomes smaller than the previous one.

19. The training apparatus as claimed in claim 17, wherein said control means is adapted to continuously receive said pulse wave data from said pulse wave measuring means during the time period when the pressure within said inflatable bag is increasing in said preprocessing, and determine, as the maximum pulse wave pressure, an immediately preceding gas pressure within said inflatable bag when said pulse wave data indicates that said magnitude of the pulse wave component becomes smaller than the previous one.

20. The training apparatus as claimed in claim 1, wherein said pulse wave measuring means is adapted to measure the gas pressure within said inflatable bag as said parameter.

\* \* \* \* \*